(12) United States Patent
Engelhardt et al.

(10) Patent No.: US 10,196,445 B1
(45) Date of Patent: Feb. 5, 2019

(54) IPILIMUMAB VARIANT WITH ENHANCED ADCC

(71) Applicant: Bristol-Myers Squibb Company, Princeton, NJ (US)

(72) Inventors: John J. Engelhardt, Fremont, CA (US); Alan J. Korman, Piedmont, CA (US); Mark J. Selby, San Francisco, CA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 189 days.

(21) Appl. No.: 15/071,489

(22) Filed: Mar. 16, 2016

Related U.S. Application Data

(60) Provisional application No. 62/134,146, filed on Mar. 17, 2015.

(51) Int. Cl.
| | | |
|---|---|---|
| *C07K 16/28* | (2006.01) | |
| *A61K 39/395* | (2006.01) | |
| *C07K 16/32* | (2006.01) | |
| *A61K 39/00* | (2006.01) | |

(52) U.S. Cl.
CPC .... *C07K 16/2818* (2013.01); *A61K 39/39558* (2013.01); *C07K 16/32* (2013.01); *A61K 2039/505* (2013.01); *C07K 2317/21* (2013.01); *C07K 2317/565* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 5,977,318 A | 11/1999 | Linsley et al. | |
| 6,682,736 B1 | 1/2004 | Hanson et al. | |
| 6,984,720 B1 | 1/2006 | Korman et al. | |
| 7,605,238 B2 | 10/2009 | Korman et al. | |
| 8,871,204 B2 | 10/2014 | Brezski et al. | |
| 2010/0173323 A1* | 7/2010 | Strome | C07K 16/2863 435/7.1 |
| 2010/0317834 A1* | 12/2010 | Lazar | C07K 16/00 530/387.1 |
| 2013/0243731 A1* | 9/2013 | Dias | A61K 35/761 424/93.2 |
| 2014/0065142 A1* | 3/2014 | Roschke | C07K 16/2848 424/134.1 |
| 2014/0370013 A1* | 12/2014 | Desjarlais | C07K 16/2809 424/135.1 |
| 2015/0152183 A1* | 6/2015 | Chamberlain | C07K 16/082 530/387.9 |
| 2015/0353637 A1* | 12/2015 | Wang | C07K 16/2863 424/139.1 |

FOREIGN PATENT DOCUMENTS

| | | |
|---|---|---|
| WO | WO 2006/104989 A2 | 10/2006 |
| WO | WO 2014/089113 A1 | 6/2014 |

OTHER PUBLICATIONS

Selby M J et al. (2013) Cancer Immunol Res; 1(1); 32-42.*
Simpson T R et al. (2013) J Exp Med 210: 1695-710.*
Lazar G A et al. (2006) Proc Natl Acad Sci USA 103:4005-10.*
Natsume A et al. (2009) Drug Des Devel Ther 3: 7-16.*
Moore et al. (2010) mAbs 2:2, 181-189.*
Marcello Albanesi et al., *Journal of Immunology*, "Cutting Edge: FcγRIII (CD16) and FcγRI (CD64) Are Responsible for Anti-Glycoprotein 75 Monoclonal Antibody TA99 Therapy for Experimental Metastatic B16 Melanoma", 189: pp. 5513-5517, 2012.
Lisette Bevaart et al., *Cancer Res*, "The High-Affinity IgG Receptor, FCγRI, Plays a Central Role in Antibody Therapy of Experimental Melanoma", vol. 66 (3), pp. 1261-1264, 2006.
Brigitte Birebent et al, Eur. *J. Immunology*, "Suppressive Properties of Human $CD4^+CD25^+$ Regulatory T Cells are Dependent on CTLA-4 Expression", vol. 34, pp. 3485-3496, 2004.
Stylianos Bournazos et al., *Cell*, "Broadly Neutralizing Anti-HIV-1 Antibodies Require Fc Effector Functions for in Vivo Activity", vol. 158, pp. 1243-1253, 2014.
F. Stephen Hodi et al., *PNAS* "Immunologic and Clinical Effects of antibody Blockade of Cytotoxic T Lymphocyte-associated Antigen 4 in Previously Vaccinated Cancer Patients", vol. 105, pp. 3005-3010, 2008.
Deborah J. Lenschow et al., *Annu. Rev. Immunol.*, "CD28/B7 System of T Cell Costimulation", vol. 14, pp. 233-258, 1996.
Chrysoula Liakou et al., *PNAS*, "CTLA-4 Blockage Increases IFNγ-Producing $CD4^+ICOS^{hi}$ Cells to Shift the Ratio of Effector to Regulatory T Cells in Cancer Patients", vol. 105: pp. 14987-14992 2008.
Ajay V. Maker et al, *Journal of Immunology*, "Analysis of the Cellular Mechanism of Antitumor Responses and Autoimmunity in Patients Treated with CTLA-4 Blockade", vol. 175, pp. 7746-7754, 2005.
Falk Nimmerjahn et al., *Immunological Reviews*, "Antibody-Mediated Modulation of Immune Responses", vol. 236: pp. 265-275, 2010.
Falk Nimmerjahn et al., *Science*, "Divergent Immunoglobulin G Subclass Activity Through Selective Fc Receptor Binding", vol. 310: pp. 1510-1512, 2005.
Falk Nimmerjahn et al., *Nature Reviews Immunol.*, "Fcγ Receptors as Regulators of Immune Responses", vol. 8: pp. 34-47, 2008.

(Continued)

*Primary Examiner* — Ilia I Ouspenski
(74) *Attorney, Agent, or Firm* — Gregory R. Bellomy

(57) ABSTRACT

The present invention provides anti-CTLA-4 antibodies having enhanced ADCC activity, and their use in treating cancer. In one embodiment, the anti-CTLA-4 antibody is ipilimumab, and ADCC activity is enhanced by introducing G236A, S239D, A330L and I332E mutations ("GASDALIE") into the Fc region of the heavy chain constant domain.

11 Claims, 23 Drawing Sheets

Specification includes a Sequence Listing.

(56) References Cited

OTHER PUBLICATIONS

Karl S. Peggs et al., *JEM* "Blockade of CTLA-4 on Both Effector and Regulatory T Cell Compartments Contributes to the Antitumor Activity of Anti-CTLA-4 Antibodies", vol. 206: No. 8, pp. 1717-1725, 2009.
Emanuela Romano., *J. Immunotherapy of Cancer*, "FCγRIIIA (CD16)-Expressing Monocytes Mediate the Depletion of Tumor-infiltrating Tregs via Ipilimumab-dependent ADCC in Melanoma Patients", 2 (Supp) 3): O14, pp. 1-2, 2014.
Mark J. Selby et al., *Cancer Immunology Research* "Anti-CTLA-4 Antibodies of IgG2a Isotype Enhance Antitumor Activity Through Reduction of Intratumoral Regulatory T Cells", vol. 1(1), pp. 32-42, 2013.
Patrick Smith et al., *PNAS* "Mouse Model Recapitulating Human Fcγ Receptor Structural and Functional Diversity", vol. 109, pp. 6181-6186, 2012.
Takeshi Takahashi et al., *JEM* "Immunologic Self-Tolerance Maintained by $CD25^+CD4^+$ Regulatory T Cells Constitutively Expressing Cytotoxic T. Lymphocyte-associated Antigen 4", vol. 192: No. 2, pp. 303-309, 2000.
Kajsa Wing et al., *Science* "CTLA-4 Control Over $Foxp3^+$ Regulatory T Cell Function", vol. 322, pp. 271-275, 2008.

\* cited by examiner

A.

B.

C.

D.

A.

B.

C.

D.

A.

B.

A.

B.

D. 9D9 g2b NF

E. 9D9 mg2a

F. 9D9 mg2a NF

A.

B.

A.

B.

C.

D.

A.

B.

3/9 TF

C.

D.

A.

B.

C.

D.

A.

B.

C.

D.

A.

B.

C.

D.

SEQUENCE LISTING

<160> NUMBER OF SEQ ID NOS: 15

<210> SEQ ID NO 1
<211> LENGTH: 223
<212> TYPE: PRT
<213> ORGANISM: Homo sapiens

<400> SEQUENCE: 1

```
Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
                20                  25                  30

Val Phe Cys Lys Ala Met His Val Ala Gln Pro Ala Val Val Leu Ala
                35                  40                  45

Ser Ser Arg Gly Ile Ala Ser Phe Val Cys Glu Tyr Ala Ser Pro Gly
            50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
                100                 105                 110

Asn Leu Thr Ile Gln Gly Leu Arg Ala Met Asp Thr Gly Leu Tyr Ile
            115                 120                 125

Cys Lys Val Glu Leu Met Tyr Pro Pro Pro Tyr Tyr Leu Gly Ile Gly
            130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
                180                 185                 190

Arg Ser Pro Leu Thr Thr Gly Val Tyr Val Lys Met Pro Pro Thr Glu
            195                 200                 205

Pro Glu Cys Glu Lys Gln Phe Gln Pro Tyr Phe Ile Pro Ile Asn
            210                 215                 220
```

<210> SEQ ID NO 2
<211> LENGTH: 220
<212> TYPE: PRT
<213> ORGANISM: Homo sapiens

<400> SEQUENCE: 2

```
Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
                20                  25                  30

Asp Asn Ala Val Asn Leu Ser Cys Lys Tyr Ser Tyr Asn Leu Phe Ser
                35                  40                  45

Arg Glu Phe Arg Ala Ser Leu His Lys Gly Leu Asp Ser Ala Val Glu
            50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
```

```
                100              105              110
Lys Ile Glu Val Met Tyr Pro Pro Tyr Leu Asp Asn Glu Lys Ser
            115              120              125
Asn Gly Thr Ile Ile His Val Lys Gly Lys His Leu Cys Pro Ser Pro
            130              135              140
Leu Phe Pro Gly Pro Ser Lys Pro Phe Trp Val Leu Val Val Val Gly
145              150              155              160
Gly Val Leu Ala Cys Tyr Ser Leu Leu Val Thr Val Ala Phe Ile Ile
                165              170              175
Phe Trp Val Arg Ser Lys Arg Ser Arg Leu Leu His Ser Asp Tyr Met
                180              185              190
Asn Met Thr Pro Arg Arg Pro Gly Pro Thr Arg Lys His Tyr Gln Pro
            195              200              205
Tyr Ala Pro Pro Arg Asp Phe Ala Ala Tyr Arg Ser
        210              215              220
```

<210> SEQ ID NO 3
<211> LENGTH: 5
<212> TYPE: PRT
<213> ORGANISM: Homo sapiens

<400> SEQUENCE: 3

Ser Tyr Thr Met His
1               5

<210> SEQ ID NO 4
<211> LENGTH: 17
<212> TYPE: PRT
<213> ORGANISM: Homo sapiens

<400> SEQUENCE: 4

Phe Ile Ser Tyr Asp Gly Asn Asn Lys Tyr Tyr Ala Asp Ser Val Lys
1               5               10              15
Gly

<210> SEQ ID NO 5
<211> LENGTH: 9
<212> TYPE: PRT
<213> ORGANISM: Homo sapiens

<400> SEQUENCE: 5

Thr Gly Trp Leu Gly Pro Phe Asp Tyr
1               5

<210> SEQ ID NO 6
<211> LENGTH: 12
<212> TYPE: PRT
<213> ORGANISM: Homo sapiens

<400> SEQUENCE: 6

Arg Ala Ser Gln Ser Val Gly Ser Ser Tyr Leu Ala
1               5               10

<210> SEQ ID NO 7
<211> LENGTH: 7
<212> TYPE: PRT
<213> ORGANISM: Homo sapiens

<400> SEQUENCE: 7

Gly Ala Phe Ser Arg Ala Thr
1               5

```
<210> SEQ ID NO 8
<211> LENGTH: 9
<212> TYPE: PRT
<213> ORGANISM: Homo sapiens

<400> SEQUENCE: 8

Gln Gln Tyr Gly Ser Ser Pro Trp Thr
1               5

<210> SEQ ID NO 9
<211> LENGTH: 118
<212> TYPE: PRT
<213> ORGANISM: Homo sapiens

<400> SEQUENCE: 9

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser
        115

<210> SEQ ID NO 10
<211> LENGTH: 108
<212> TYPE: PRT
<213> ORGANISM: Homo sapiens

<400> SEQUENCE: 10

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 11
<211> LENGTH: 448
<212> TYPE: PRT
<213> ORGANISM: Homo sapiens
```

<400> SEQUENCE: 11

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Thr Met His Trp Val Arg Gln Ala Pro Gly Lys Gly Leu Glu Trp Val
         35                  40                  45

Thr Phe Ile Ser Tyr Asp Gly Asn Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Ile Tyr Tyr Cys
                 85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415
```

-continued

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445

<210> SEQ ID NO 12
<211> LENGTH: 447
<212> TYPE: PRT
<213> ORGANISM: Homo sapiens

<400> SEQUENCE: 12

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu

```
                    340                 345                 350
        Pro Pro Ser Arg Asp Glu Leu Thr Lys Asn Gln Val Ser Leu Thr Cys
                355                 360                 365
        Leu Val Lys Gly Phe Tyr Pro Ser Asp Ile Ala Val Glu Trp Glu Ser
                370                 375                 380
        Asn Gly Gln Pro Glu Asn Asn Tyr Lys Thr Thr Pro Pro Val Leu Asp
        385                 390                 395                 400
        Ser Asp Gly Ser Phe Phe Leu Tyr Ser Lys Leu Thr Val Asp Lys Ser
                        405                 410                 415
        Arg Trp Gln Gln Gly Asn Val Phe Ser Cys Ser Val Met His Glu Ala
                        420                 425                 430
        Leu His Asn His Tyr Thr Gln Lys Ser Leu Ser Leu Ser Pro Gly
                        435                 440                 445

<210> SEQ ID NO 13
<211> LENGTH: 215
<212> TYPE: PRT
<213> ORGANISM: Homo sapiens

<400> SEQUENCE: 13

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 14
<211> LENGTH: 448
<212> TYPE: PRT
<213> ORGANISM: Artificial Sequence
<220> FEATURE:
<223> OTHER INFORMATION: human anti-CTLA-4 mAb ipilimumab heavy chain
      with G236A/S239D/A330L/I332E changes
```

<400> SEQUENCE: 14

```
Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Thr Met His Trp Val Arg Gln Ala Pro Gly Lys Gly Leu Glu Trp Val
        35                  40                  45
Thr Phe Ile Ser Tyr Asp Gly Asn Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Ile Tyr Tyr Cys
                85                  90                  95
Ala Arg Thr Gly Trp Leu Gly Pro Phe Asp Tyr Trp Gly Gln Gly Thr
            100                 105                 110
Leu Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Arg Val Glu Pro Lys Ser Cys Asp Lys Thr
    210                 215                 220
His Thr Cys Pro Pro Cys Pro Ala Pro Glu Leu Leu Ala Gly Pro Asp
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Leu Pro Glu Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
```

```
Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445

<210> SEQ ID NO 15
<211> LENGTH: 447
<212> TYPE: PRT
<213> ORGANISM: Artificial Sequence
<220> FEATURE:
<223> OTHER INFORMATION: human anti-CTLA-4 mAb ipilimumab heavy chain
      with G236A/S239D/A330L/I332E changes and lacking C-terminal K

<400> SEQUENCE: 15

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Ala Gly Pro Asp
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Leu Pro Glu Glu Lys Thr
```

```
                    325                 330                 335
Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
        370             375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly
            435                 440                 445
```

IPILIMUMAB VARIANT WITH ENHANCED ADCC

CROSS-REFERENCE TO RELATED APPLICATIONS

This application claims the benefit under 35 U.S.C. § 119(e) of U.S. Provisional Application No. 62/134,146, filed 17 Mar. 2015, the disclosure of which is incorporated herein by reference.

SEQUENCE LISTING

The Sequence Listing filed electronically herewith is also hereby incorporated by reference in its entirety (File Name: 20160316_SEQL_12487USNP_GB.txt; Date Created: 11 Mar. 2016; File Size: 24.2 KB).

BACKGROUND OF THE INVENTION

The immune system is capable of controlling tumor development and mediating tumor regression. This requires the generation and activation of tumor antigen-specific T cells. Multiple T-cell co-stimulatory receptors and T-cell negative regulators, or co-inhibitory receptors, act in concert to control T-cell activation, proliferation, and gain or loss of effector function. Among the earliest and best characterized T-cell co-stimulatory and co-inhibitory molecules are CD28 and CTLA-4. Rudd et al. (2009) *Immunol. Rev.* 229: 12. CD28 provides co-stimulatory signals to T-cell receptor engagement by binding to B7-1 and B7-2 ligands on antigen-presenting cells, while CTLA-4 provides a negative signal down-regulating T-cell proliferation and function. CTLA-4, which also binds the B7-1 (CD80) and B7-2 (CD86) ligands but with higher affinity than CD28, acts as a negative regulator of T-cell function through both cell autonomous (or intrinsic) and cell non-autonomous (or extrinsic) pathways. Intrinsic control of CD8 and CD4 T effector ($T_{eff}$) function is mediated by the inducible surface expression of CTLA-4 as a result of T-cell activation, and inhibition of T-cell proliferation and cytokine proliferation by multivalent engagement of B7 ligands on opposing cells. Peggs et al. (2008) *Immunol. Rev.* 224:141.

Anti-CTLA-4 antibodies, when cross-linked, suppress T cell function in vitro. Krummel & Allison (1995) *J. Exp. Med.* 182:459; Walunas et al. (1994) *Immunity* 1:405. Regulatory T cells ($T_{regs}$), which express CTLA-4 constitutively, control effector T cell ($T_{eff}$) function in a non-cell autonomous fashion. $T_{regs}$ that are deficient for CTLA-4 have impaired suppressive ability (Wing et al. (2008) *Science* 322:271) and antibodies that block CTLA-4 interaction with B7 can inhibit $T_{reg}$ function (Read et al. (2000) *J. Exp. Med.* 192:295; Quezada et al. (2006) *J. Clin. Invest.* 116:1935). More recently, $T_{effs}$ have also been shown to control T cell function through extrinsic pathways (Corse & Allison (2012) *J. Immunol.* 189:1123; Wang et al. (2012) *J. Immunol.* 189:1118). Extrinsic control of T cell function by $T_{regs}$ and $T_{effs}$ occurs through the ability of CTLA-4-positive cells to remove B7 ligands on antigen-presenting cells, thereby limiting their co-stimulatory potential. Qureshi et al. (2011) *Science* 332: 600; Onishi et al. (2008) *Proc. Nat'l Acad. Sci. (USA)* 105:10113. Antibody blockade of CTLA-4/B7 interactions is thought to promote $T_{eff}$ activation by interfering with negative signals transmitted by CTLA-4 engagement; this intrinsic control of T-cell activation and proliferation can promote both $T_{eff}$ and $T_{reg}$ proliferation (Krummel & Allison (1995) *J. Exp. Med.* 182:459; Quezada et al. (2006) *J. Clin. Invest.* 116:1935). In early studies with animal models, antibody blockade of CTLA-4 was shown to exacerbate autoimmunity. Perrin et al. (1996) *J. Immunol.* 157: 1333; Hurwitz et al. (1997) *J. Neuroimmunol.* 73:57. By extension to tumor immunity, the ability of anti-CTLA-4 to cause regression of established tumors provided a dramatic example of the therapeutic potential of CTLA-4 blockade. Leach et al. (1996) *Science* 271:1734.

Human antibodies to human CTLA-4, ipilimumab and tremelimumab, were selected to inhibit CTLA-4-B7 interactions (Keler et al. (2003) *J. Immunol.* 171:6251; Ribas et al. (2007) *Oncologist* 12:873) and have been tested in a variety of clinical trials for multiple malignancies. Hoos et al. (2010) *Semin. Oncol.* 37:533; Ascierto et al. (2011) *J. Transl. Med.* 9:196. Tumor regressions and disease stabilization were frequently observed, and treatment with these antibodies has been accompanied by adverse events with inflammatory infiltrates capable of affecting a variety of organ systems. In 2011, ipilimumab, which has an IgG1 constant region, was approved in the US and EU for the treatment of unresectable or metastatic melanoma based on an improvement in overall survival in a phase III trial of previously treated patients with advanced melanoma. Hodi et al. (2010) *N. Engl. J. Med.* 363:711.

Recent studies have suggested that the therapeutic efficacy of anti-CTLA-4 antibodies like ipilimumab may involve depletion of regulatory T cells ($T_{regs}$). Accordingly, the need exists for anti-CTLA-4 antibodies, such as ipilimumab, having enhanced ADCC activity. Such improved anti-CTLA-4 antibodies may be more effective anti-tumor agents than current antibodies.

SUMMARY OF THE INVENTION

The present invention provides improved variants of anti-human CTLA-4 antibodies, such as ipilimumab, having mutations in the Fc region that enhance Fcγ receptor binding, and thus enhance ADCC activity, such as anti-human CTLA-4 antibodies with heavy chains comprising residues 236A, 239D, 330L and 332E according to the Kabat numbering system. In one embodiment the anti-human CTLA-4 antibody is ipilimumab and comprises heavy chain modifications G236A, S239D, A330L and I332E ("ipilimumab-GASDALIE").

In one embodiment the improved ipilimumab comprises one or more heavy chains comprising the sequence of SEQ ID NO: 14 and one or more light chains comprising the sequence of SEQ ID NO: 13. In another embodiment the improved ipilimumab comprises one or more heavy chains comprising the sequence of SEQ ID NO: 15 (lacking the C-terminal lysine residue) and one or more light chains comprising the sequence of SEQ ID NO: 13.

In another aspect the invention provides methods of treatment comprising administration of an improved anti-CTLA-4 antibody of the present invention, such as ipilimumab-GASDALIE, to a human subject in need thereof. In one embodiment the treatment is treatment of cancer, including but not limited to, unresectable or metastatic melanoma.

In various embodiments, treatment is in combination with one or more other anti-tumor therapeutic agents, including other immunomodulatory agents.

In other embodiments, ipilimumab-GASDALIE is administered at doses lower than those approved for treatment of the same indication with ipilimumab.

BRIEF DESCRIPTION OF THE DRAWINGS

FIG. 1A, control mouse IgG (human anti-diphtheria toxin antibody with a mouse IgG1 isotype, also used as the control in other experiments); FIG. 1B, anti-CTLA-4-γ1D265A; FIG. 1C, anti-CTLA-4-γ2b; FIG. 1D, anti-CTLA-4-γ2a. The number of tumor-free (TF) mice per group is shown for each group of 10 mice. See Example 1 (derived from example 2 of WO 2014/089113).

FIG. 2A, control mouse IgG1 antibody; FIG. 2B, anti-CTLA-4 IgG1; FIG. 2C, anti-CTLA-4 IgG1D265A; FIG. 2D, anti-CTLA-4 IgG2a; FIG. 2E, anti-CTLA-4 IgG2b. See Example 2 (derived from example 4 of WO 2014/089113).

FIG. 4A, control mouse IgG1 antibody; FIG. 4B, anti-CTLA-4 IgG2a; FIG. 4C, anti-CTLA-4 IgG1D265A. See Example 3 (derived from example 6 of WO 2014/089113).

FIG. 6A, control mouse IgG1 antibody; FIG. 6B, anti-CTLA-4 IgG1D265A; FIG. 6C, anti-CTLA-4 IgG2b; FIG. 6D, non-fucosylated (NF) anti-CTLA-4 IgG2b; FIG. 6E, anti-CTLA-4 IgG2a; FIG. 6F, anti-CTLA-4 IgG2a-NF. The number of TF mice per group is shown for each group of 12 mice. See Example 4 (derived from example 13 of WO 2014/089113).

FIG. 8A shows a titration of ipilimumab (lower curve) and a non-fucosylated variant of ipilimumab (upper curve), compared with an isotype control (data points), in an assay of the ability of cell line NK92 to induce specific lysis of 58 α-β-CTLA4 CD3 zeta expressing cell line. See Example 5. Non-fucosylated Fc increases lytic activity of ipilimumab, reducing the $EC_{50}$ from 0.13 ng/ml to 0.0056 ng/ml. In FIGS. 8B-8E, both the NK cells and the target cells were isolated from samples from human subjects, and antibodies are at 1 μg/ml, and lysis is measured by two hour calcein release assay. See Example 6. FIG. 8B shows specific lysis of $CD4^+$ T cells as a function of the ratio of activated NK cells to target cells, in the presence of ipilimumab (CTLA4-IgG1) (triangles; one of the bottom lines), non-fucosylated ipilimumab (diamonds; uppermost line), a PD-L1 antibody (12A4) (circles; middle line), and an IgG1 isotype control (squares; one of the bottom lines). FIGS. 8C-8E show specific lysis of $CD4^+$ T cells, $CD8^+$ T cells, and $T_{regs}$, respectively, by activated NK cells (10:1 effector to target cell ratio) in the presence ipilimumab (CTLA4-IgG1) (leftmost bar), non-fucosylated ipilimumab (left-middle bar), a PD-L1 antibody (12A4) (right-middle bar), and an IgG1 isotype control (rightmost bar). The results show that non-fucosylated ipilimumab is far more effective at inducing lysis of $CD4^+$ T cells and $T_{regs}$ than the unmodified IgG1 ipilimumab, but that it does not induce lysis of $CD8^+$ T cells to the same extent.

FIGS. 11A and 11B show that $T_{regs}$ (Foxp3+) are reduced in animals treated with antibodies having enhanced effector function (non-fucosylated and GASDALIE), whereas FIG. 11D shows that $CD4^+$ effector T cells are not. FIG. 11C shows that $CD8^+$ effector T cells are increased in animals treated with antibodies having enhanced effector function, perhaps as a downstream consequence of $T_{reg}$ depletion.

DETAILED DESCRIPTION OF THE INVENTION

Definitions

Figure 1A:
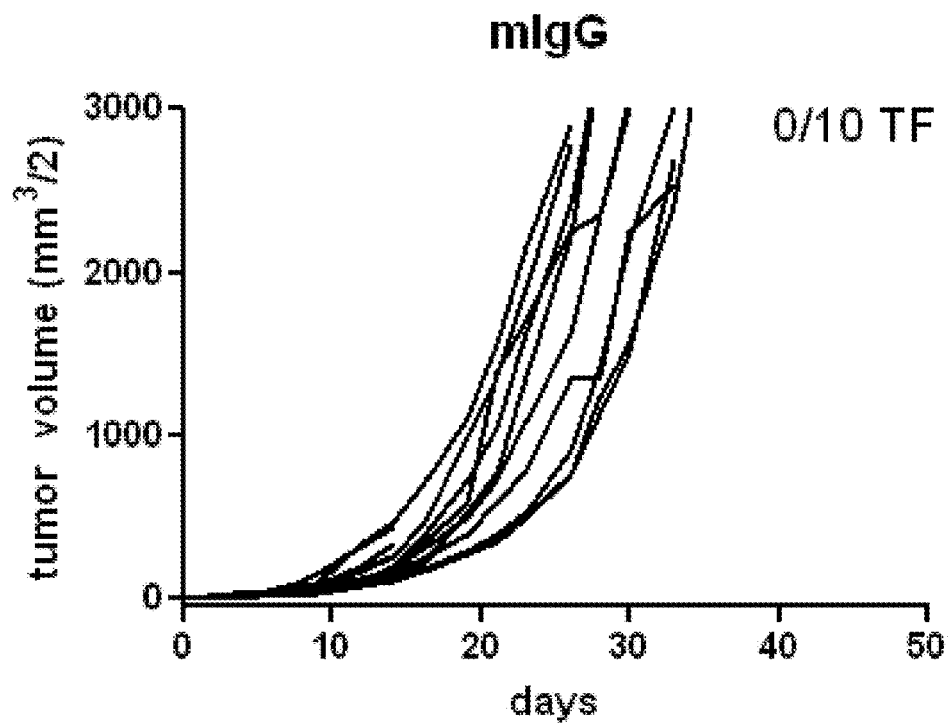
FIGS. 1A-1D (FIG. 3 of WO 2014/089113) shows the effects of different isotypes of the mouse anti-mouse CTLA-4 antibody, 9D9, on anti-tumor activity in a syngeneic CT26 adenocarcinoma mouse model.
Figure 1B:
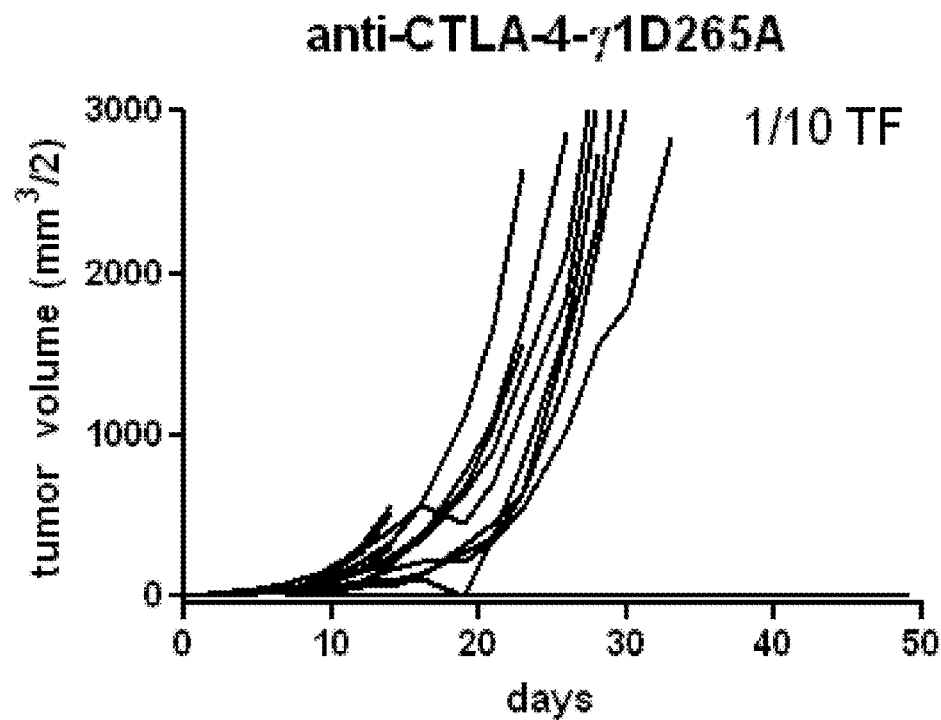
Figure 1C:
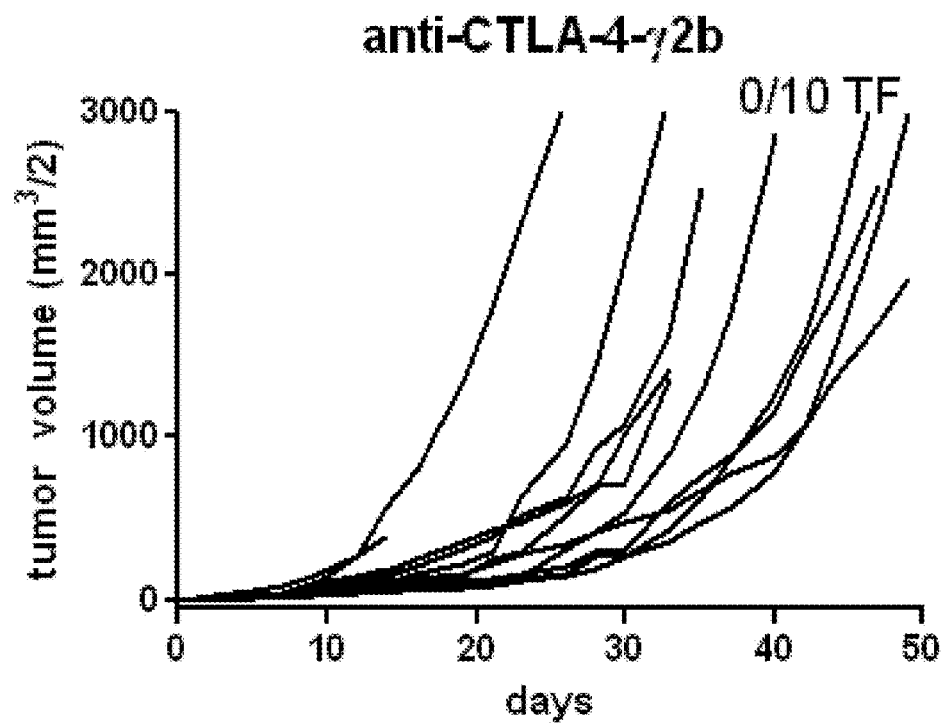
Figure 1D:
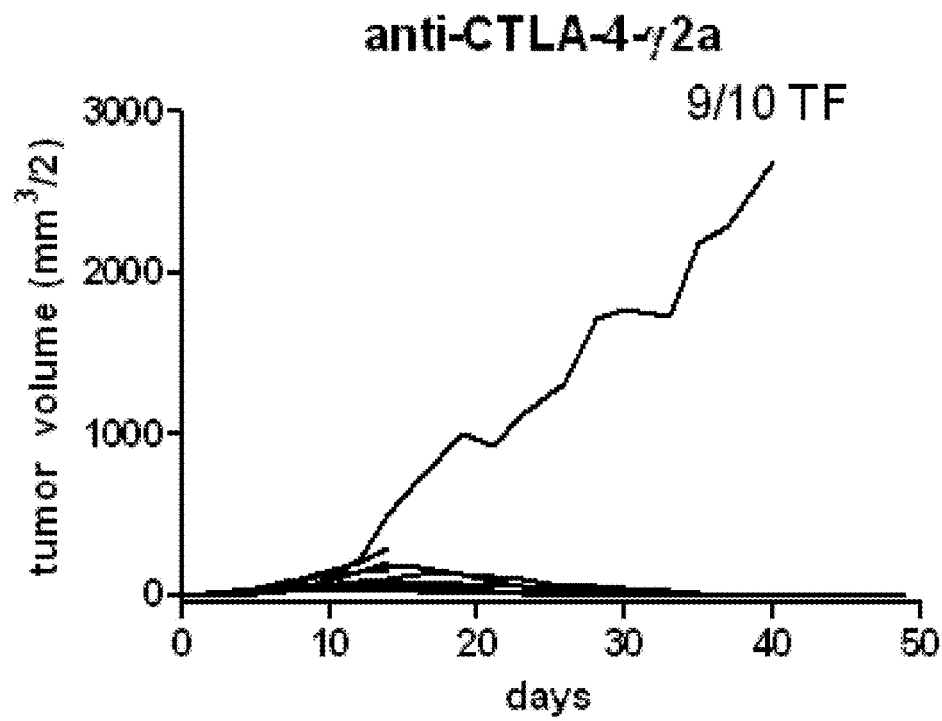
Figure 2A:
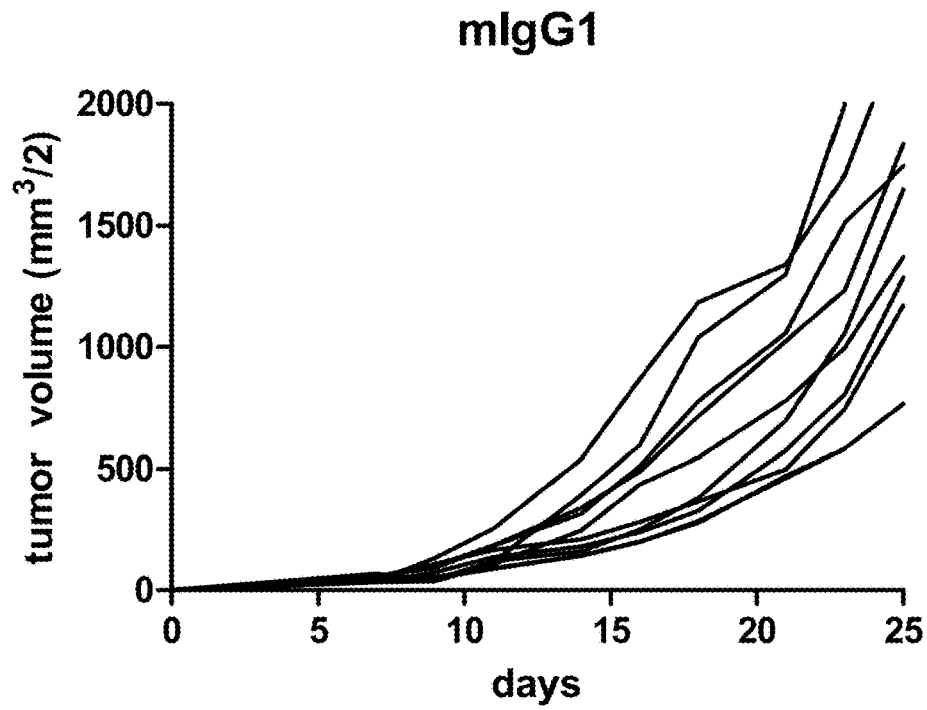
FIGS. 2A-2E (FIG. 7 of WO 2014/089113) shows the anti-tumor activity of four different mouse anti-CTLA-4 isotypes, as measured by changes in the tumor volumes in individual mice treated with these isotypes, in a MC38 colon adenocarcinoma tumor model.
Figure 2B:
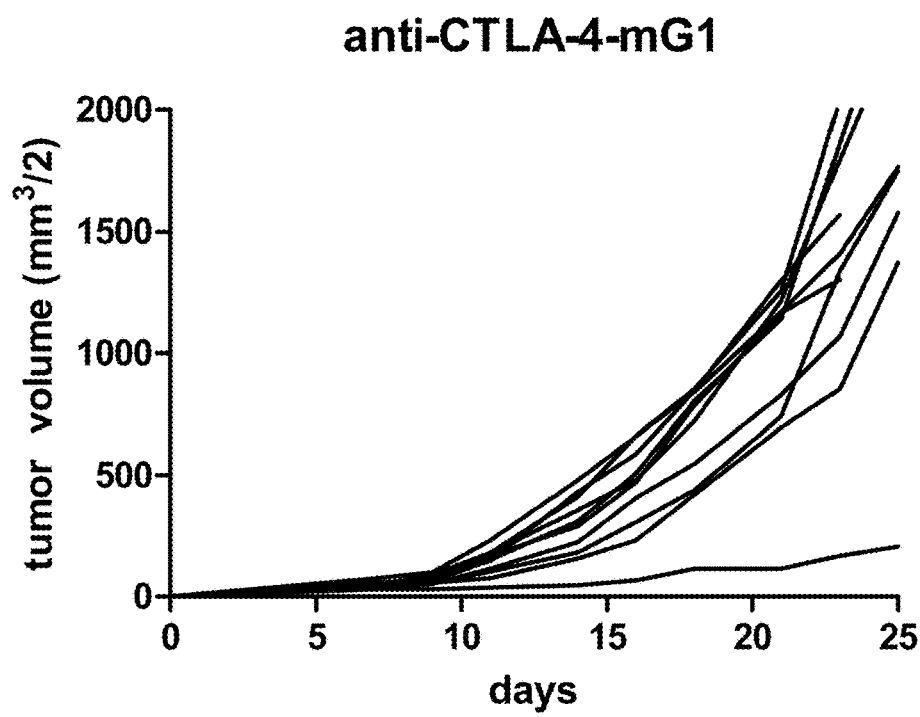
Figure 2C:
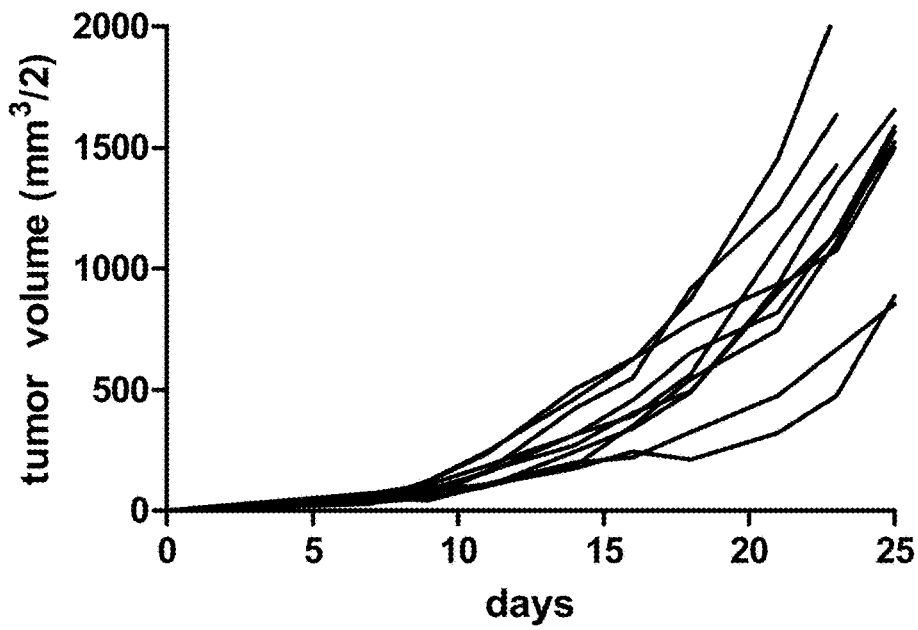
Figure 2D:
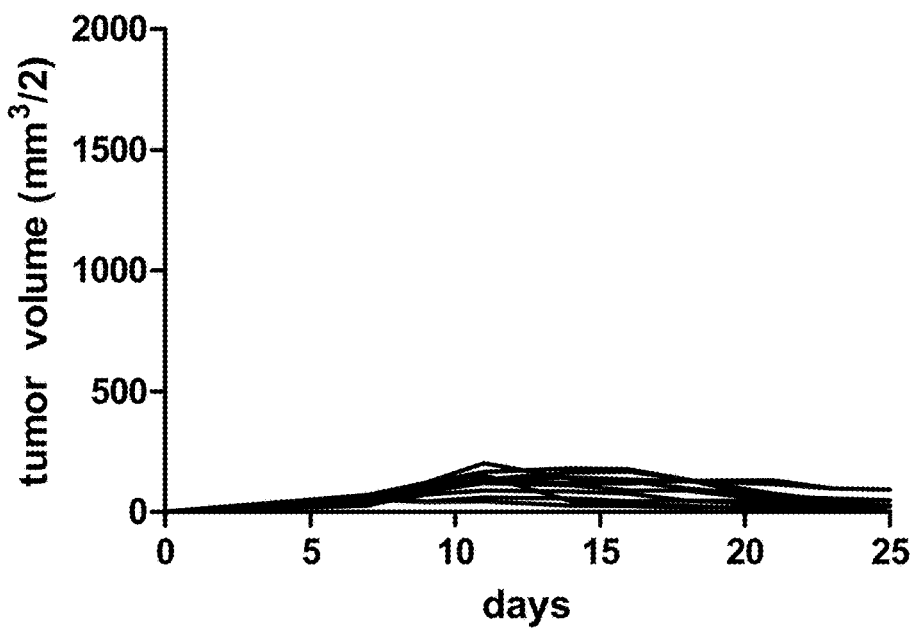
Figure 2E:
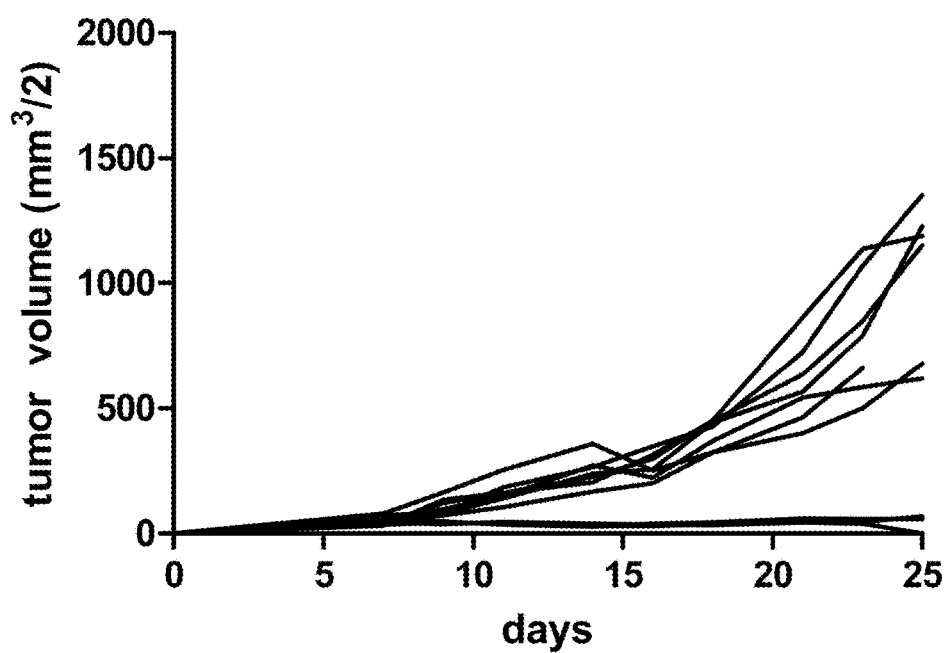
Figure 3A:
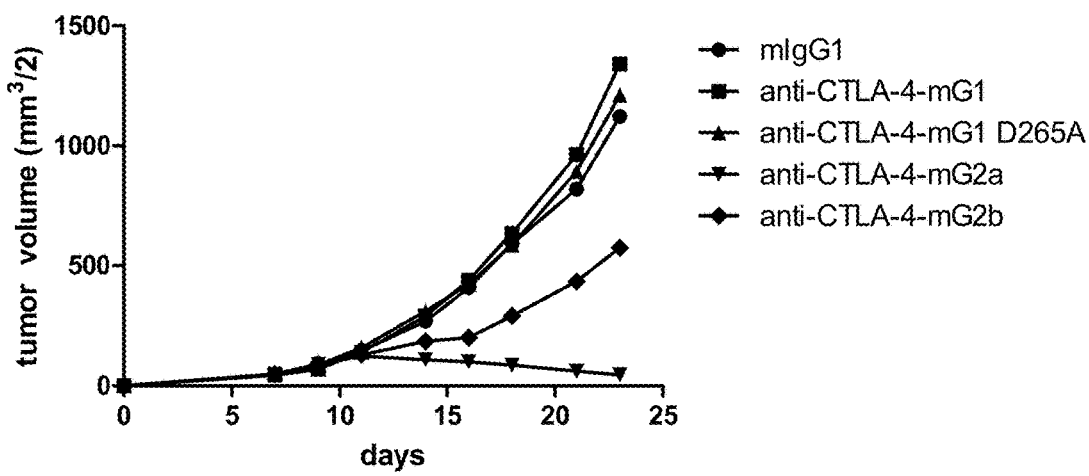
FIGS. 3A-3B (FIG. 8 of WO 2014/089113) shows the changes in mean tumor volumes (FIG. 3A) and median tumor volumes (FIG. 3B) of syngeneic MC38 colon adenocarcinoma tumors in groups of mice treated with mouse anti-CTLA-4 antibodies of different isotypes. See Example 2 (derived from example 4 of WO 2014/089113).
Figure 3B:
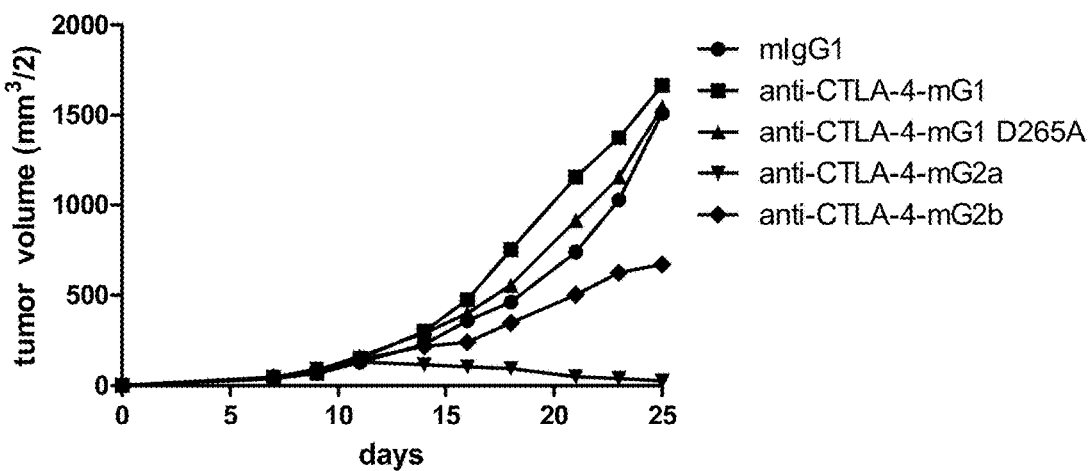
Figure 4A:
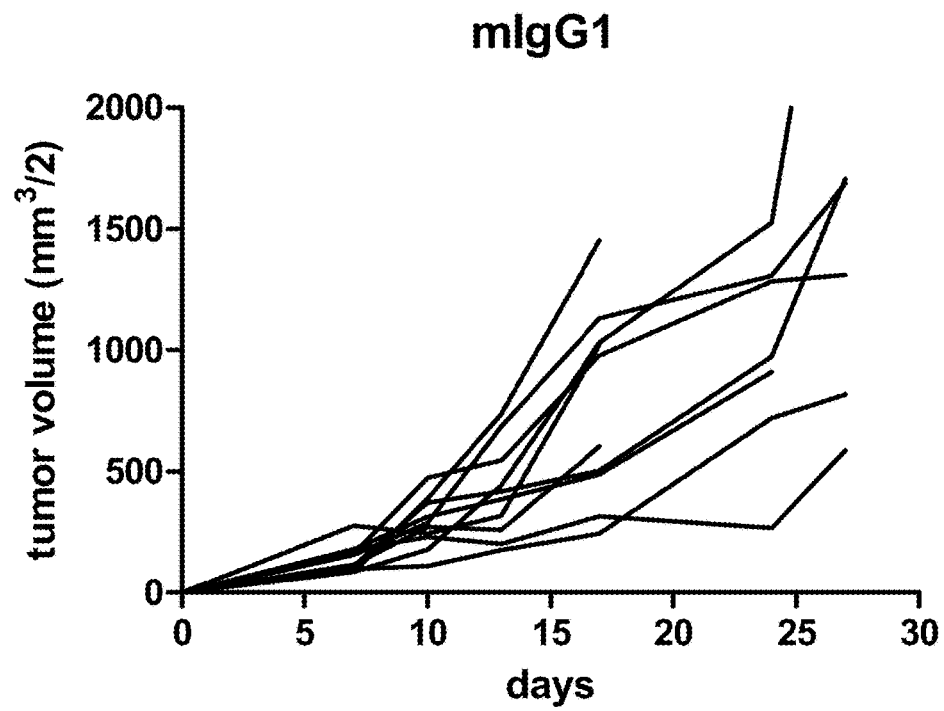
FIGS. 4A-4C (FIG. 11 of WO 2014/089113) shows the anti-tumor activity of different mouse anti-CTLA-4 isotypes in a syngeneic Sa1N fibrosarcoma mouse model as measured by the changes in tumor volumes of individual mice treated with these isotypes.
Figure 4B:
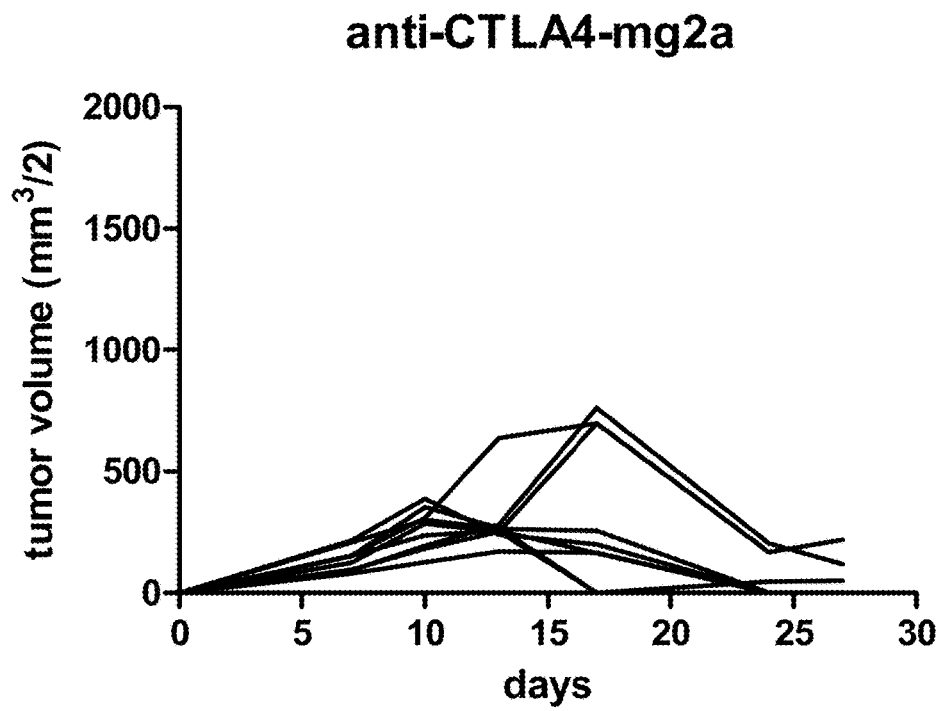
Figure 4C:
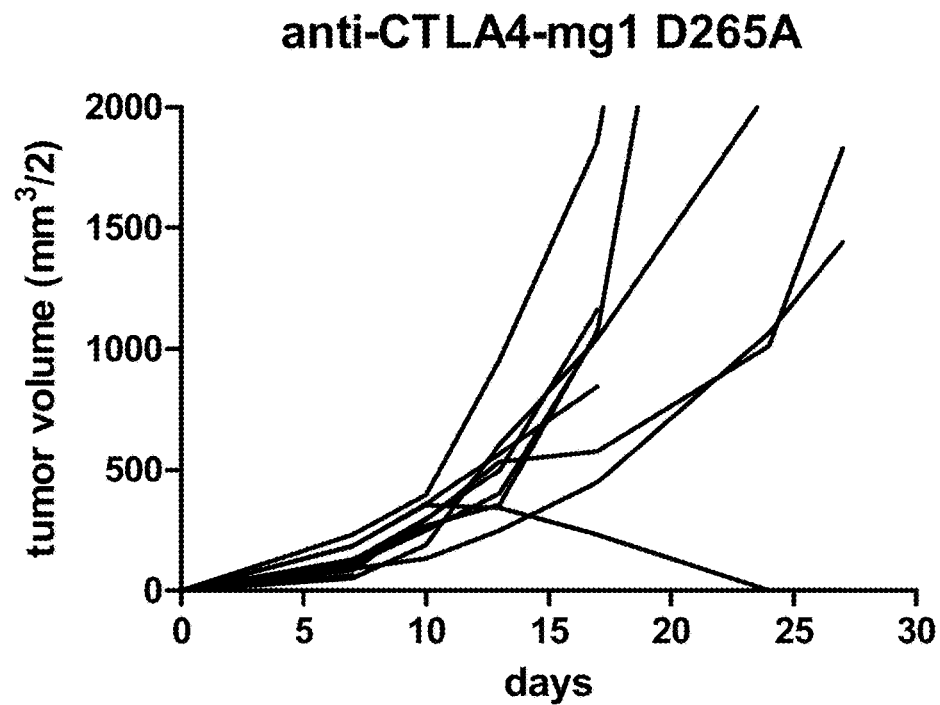
Figure 5A:
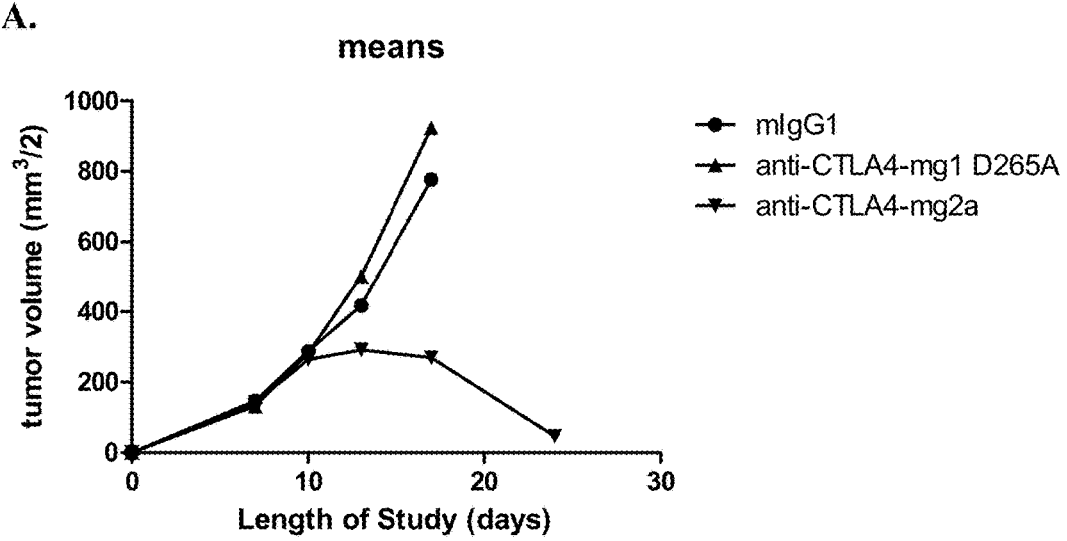
FIGS. 5A-5B (FIG. 12 of WO 2014/089113) shows the changes in mean (FIG. 5A) and median tumor volumes (FIG. 5B) of syngeneic Sa1N fibrosarcoma tumors in groups of mice treated with mouse anti-CTLA-4 antibodies of different isotypes. See Example 3 (derived from example 6 of WO 2014/089113).
Figure 5B:
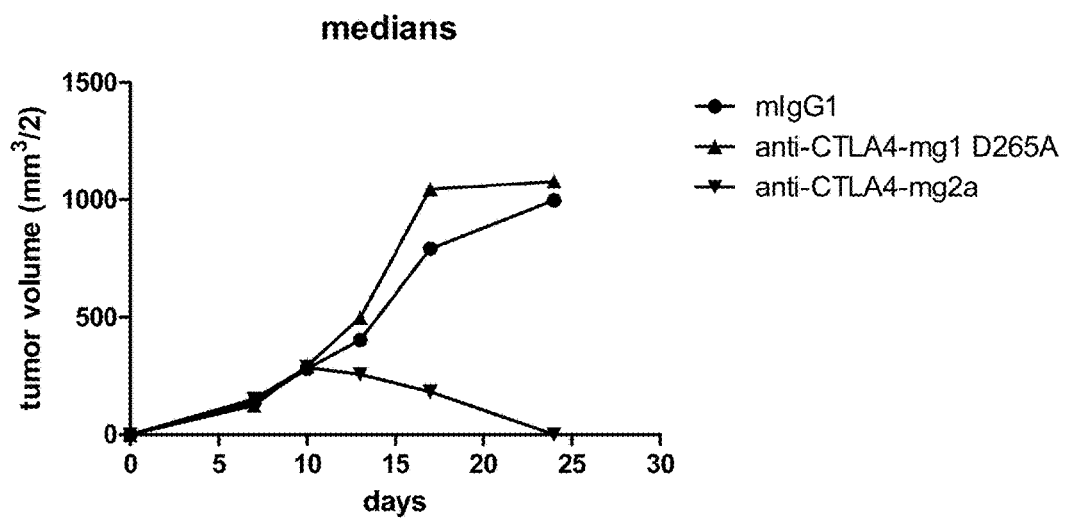
Figures 6A, 6B, 6C:
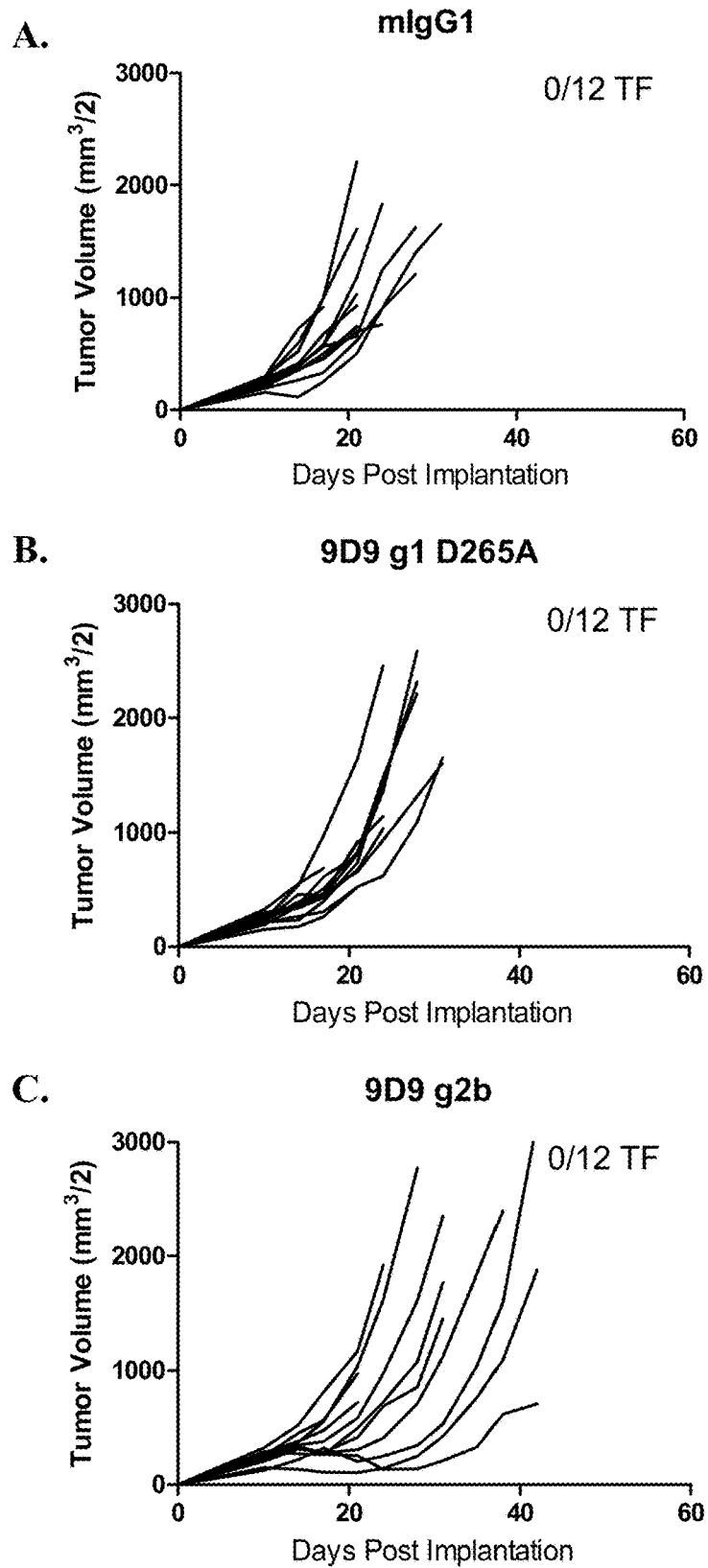
FIGS. 6A-6F (FIG. 26 of WO 2014/089113) shows the effects of afucosylation of anti-CTLA-4 (9D9) antibodies on anti-tumor activity as measured by changes in the tumor volumes in individual mice treated with these antibodies in a MC38 tumor model.
Figure 6D:
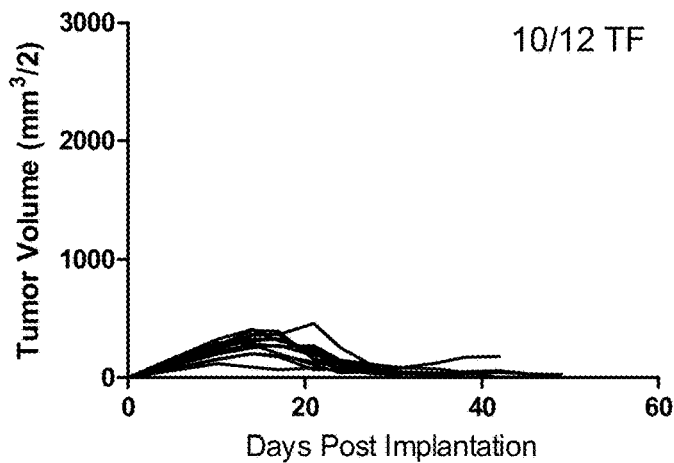
Figure 6E:
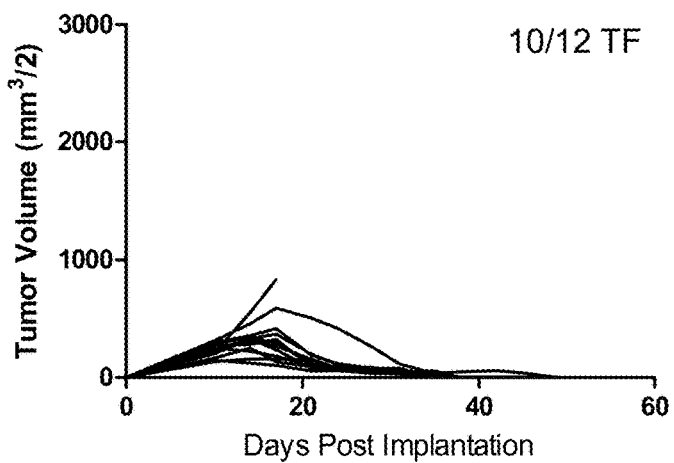
Figure 6F:
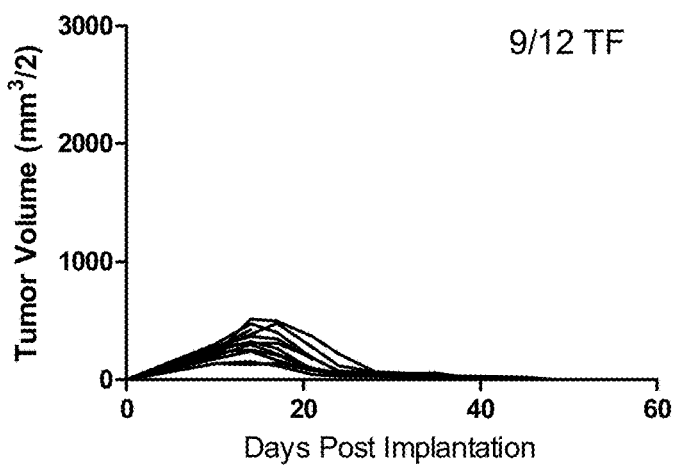
Figure 7A:
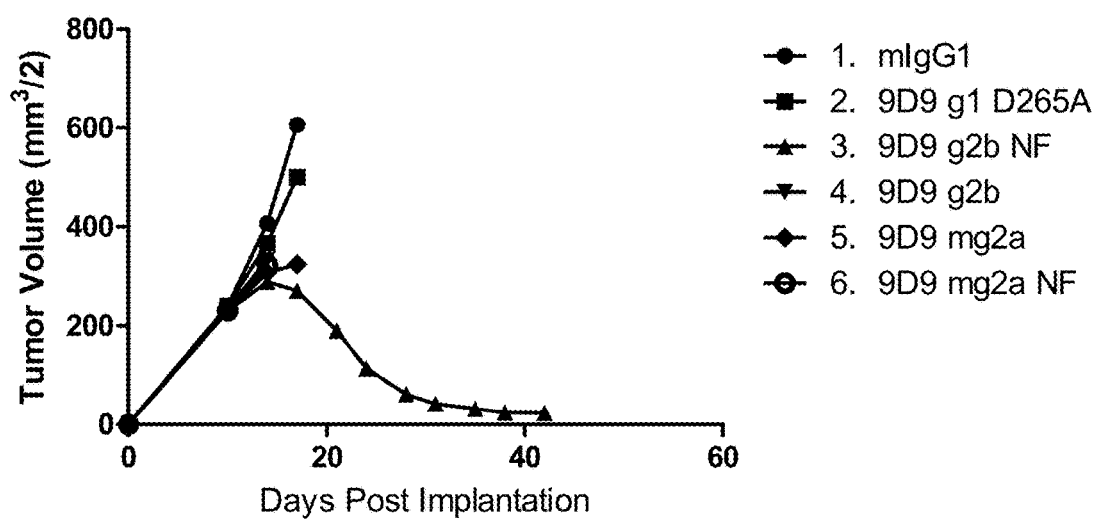
FIGS. 7A-7B (FIG. 27 of WO 2014/089113) shows the changes in mean (FIG. 7A) and median tumor volumes (FIG. 7B) of MC38 tumors in groups of mice treated with anti-CTLA-4 antibodies of different isotypes and non-fucosylated variants. See Example 4 (derived from example 13 of WO 2014/089113).
Figure 7B:
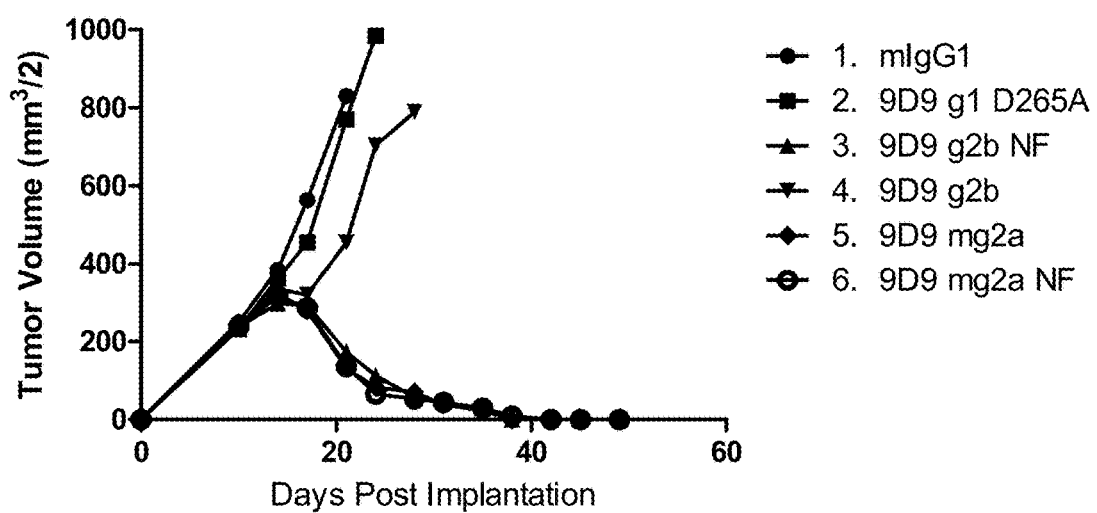

In order that the present disclosure may be more readily understood, certain terms are first defined. As used in this application, except as otherwise expressly provided herein, each of the following terms shall have the meaning set forth below. Additional definitions are set forth throughout the application.

"Administering" refers to the physical introduction of a composition comprising a therapeutic agent to a subject, using any of the various methods and delivery systems known to those skilled in the art. Preferred routes of administration for antibodies of the invention include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an antibody of the invention can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

An "antibody" (Ab) shall include, without limitation, a glycoprotein immunoglobulin which binds specifically to an antigen and comprises at least two heavy (H) chains and two light (L) chains interconnected by disulfide bonds, or an antigen-binding portion thereof. Each H chain comprises a heavy chain variable region (abbreviated herein as $V_H$) and a heavy chain constant region. The heavy chain constant region comprises three domains, $C_{H1}$, $C_{H2}$ and $C_{H3}$. Each light chain comprises a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen.

As used herein, and in accord with conventional interpretation, an antibody that is described as comprising "a" heavy chain and/or "a" light chain refers to antibodies that comprise "at least one" of the recited heavy and/or light chains, and thus will encompass antibodies having two or more heavy and/or light chains. Specifically, antibodies so described will encompass conventional antibodies having two substantially identical heavy chains and two substantially identical light chains. Antibody chains may be substantially identical but not entirely identical if they differ due to post-translational modifications, such as C-terminal cleavage of lysine residues, alternative glycosylation patterns, etc.

Unless indicated otherwise or clear from the context, an antibody defined by its target specificity (e.g. an "anti-CTLA-4 antibody") refers to antibodies that can bind to its human target (e.g. human CTLA-4). Such antibodies may or may not bind to CTLA-4 from other species.

The immunoglobulin may derive from any of the commonly known isotypes, including but not limited to IgA, secretory IgA, IgG and IgM. The IgG isotype may be divided in subclasses in certain species: IgG1, IgG2, IgG3 and IgG4 in humans, and IgG1, IgG2a, IgG2b and IgG3 in mice. IgG antibodies may be referred to herein by the symbol gamma (γ) or simply "G," e.g. IgG1 may be expressed as "γ1" or as "G1," as will be clear from the context. "Isotype" refers to the antibody class (e.g., IgM or IgG1) that is encoded by the heavy chain constant region genes. "Antibody" includes, by way of example, both naturally occurring and non-naturally occurring antibodies; monoclonal and polyclonal antibodies; chimeric and humanized antibodies; human or nonhuman antibodies; wholly synthetic antibodies; and single chain antibodies. Unless otherwise indicated, or clear from the context, antibodies disclosed herein are human IgG1 antibodies.

An "isolated antibody" refers to an antibody that is substantially free of other antibodies having different antigenic specificities (e.g., an isolated antibody that binds specifically to CTLA-4 is substantially free of antibodies that bind specifically to antigens other than CTLA-4). An isolated antibody that binds specifically to CTLA-4 may, however, cross-react with other antigens, such as CTLA-4 molecules from different species. Moreover, an isolated antibody may be substantially free of other cellular material and/or chemicals. By comparison, an "isolated" nucleic acid refers to a nucleic acid composition of matter that is markedly different, i.e., has a distinctive chemical identity, nature and utility, from nucleic acids as they exist in nature. For example, an isolated DNA, unlike native DNA, is a free-standing portion of a native DNA and not an integral part of a larger structural complex, the chromosome, found in nature. Further, an isolated DNA, unlike native DNA, can be used as a PCR primer or a hybridization probe for, among other things, measuring gene expression and detecting biomarker genes or mutations for diagnosing disease or predicting the efficacy of a therapeutic. An isolated nucleic acid may also be purified so as to be substantially free of other cellular components or other contaminants, e.g., other cellular nucleic acids or proteins, using standard techniques well known in the art.

The term "monoclonal antibody" ("mAb") refers to a preparation of antibody molecules of single molecular composition, i.e., antibody molecules whose primary sequences are essentially identical, and which exhibits a single binding specificity and affinity for a particular epitope. Monoclonal antibodies may be produced by hybridoma, recombinant, transgenic or other techniques known to those skilled in the art.

A "human" antibody (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. The terms "human" antibodies and "fully human" antibodies and are used synonymously.

A "humanized" antibody refers to an antibody having CDR regions derived from non-human animal, e.g. rodent, immunoglobulin germ line sequences in which some, most or all of the amino acids outside the CDR domains are replaced with corresponding amino acids derived from human immunoglobulins. In one embodiment of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

An "antibody fragment" refers to a portion of a whole antibody, generally including the "antigen-binding portion" ("antigen-binding fragment") of an intact antibody which retains the ability to bind specifically to the antigen bound by the intact antibody, or the Fc region of an antibody which retains FcR binding capability.

"Antibody-dependent cell-mediated cytotoxicity" ("ADCC") refers to an in vitro or in vivo cell-mediated reaction in which nonspecific cytotoxic cells that express FcRs (e.g., natural killer (NK) cells, macrophages, neutrophils and eosinophils) recognize antibody bound to a surface antigen on a target cell and subsequently cause lysis of the target cell. In principle, any effector cell with an activating FcR can be triggered to mediate ADCC.

"Cancer" refers a broad group of various diseases characterized by the uncontrolled growth of abnormal cells in the body. Unregulated cell division and growth divide and grow results in the formation of malignant tumors or cells that invade neighboring tissues and may also metastasize to distant parts of the body through the lymphatic system or bloodstream.

A "cell surface receptor" refers to molecules and complexes of molecules capable of receiving a signal and transmitting such a signal across the plasma membrane of a cell.

An "effector cell" refers to a cell of the immune system that expresses one or more FcRs and mediates one or more effector functions. Preferably, the cell expresses at least one type of an activating Fc receptor, such as, for example, human FcγRIII, and performs ADCC effector function. Examples of human leukocytes which mediate ADCC include peripheral blood mononuclear cells (PBMCs), NK cells, monocytes, macrophages, neutrophils and eosinophils.

"Effector function" refers to the interaction of an antibody Fc region with an Fc receptor or ligand, or a biochemical event that results therefrom. Exemplary "effector functions" include C1q binding, complement dependent cytotoxicity (CDC), Fc receptor binding, FcγR-mediated effector functions such as ADCC and antibody dependent cell-mediated phagocytosis (ADCP), and down-regulation of a cell surface receptor (e.g., the B cell receptor; BCR). Such effector functions generally require the Fc region to be combined with a binding domain (e.g., an antibody variable domain).

An "Fc receptor" or "FcR" is a receptor that binds to the Fc region of an immunoglobulin. FcRs that bind to an IgG antibody comprise receptors of the FcγR family, including allelic variants and alternatively spliced forms of these receptors. The FcγR family consists of three activating (FcγRI, FcγRIII, and FcγRIV in mice; FcγRIA, FcγRIIA, and FcγRIIIA in humans) receptors and one inhibitory (FcγRIIB) receptor. Various properties of human FcγRs are summarized in Table 1. The majority of innate effector cell types coexpress one or more activating FcγR and the inhibitory FcγRIIB, whereas natural killer (NK) cells selectively express one activating Fc receptor (FcγRIII in mice and FcγRIIIA in humans) but not the inhibitory FcγRIIB in mice and humans.

An "Fc region" (fragment crystallizable region) or "Fc domain" or "Fc" refers to the C-terminal region of the heavy chain of an antibody that mediates the binding of the immunoglobulin to host tissues or factors, including binding to Fc receptors located on various cells of the immune system (e.g., effector cells) or to the first component (C1q) of the classical complement system. Thus, the Fc region is a polypeptide comprising the constant region of an antibody excluding the first constant region immunoglobulin domain. In IgG, IgA and IgD antibody isotypes, the Fc region is composed of two identical protein fragments, derived from the second ($C_{H2}$) and third ($C_{H2}$) constant domains of the antibody's two heavy chains; IgM and IgE Fc regions contain three heavy chain constant domains ($C_H$ domains 2-4) in each polypeptide chain. For IgG, the Fc region comprises immunoglobulin domains Cγ2 and Cγ3 and the hinge between Cγ1 and Cγ2. Although the boundaries of the Fc region of an immunoglobulin heavy chain might vary, the human IgG heavy chain Fc region is usually defined to stretch from an amino acid residue at position C226 or P230 to the carboxy-terminus of the heavy chain, wherein the numbering is according to the EU index as in Kabat. The $C_{H2}$ domain of a human IgG Fc region extends from about amino acid 231 to about amino acid 340, whereas the $C_{H3}$ domain is positioned on C-terminal side of a $C_{H2}$ domain in an Fc region, i.e., it extends from about amino acid 341 to about amino acid 447 of an IgG. As used herein, the Fc region may be a native sequence Fc or a variant Fc. Fc may also refer to this region in isolation or in the context of an Fc-comprising protein polypeptide such as a "binding protein comprising an Fc region," also referred to as an "Fc fusion protein" (e.g., an antibody or immunoadhesin).

TABLE 1

| Properties of Human FcγRs | | | | |
|---|---|---|---|---|
| Fcγ variants | Allelic human | Affinity for IgG | Isotype preference | Cellular distribution |
| FcγRI | None described | High ($K_D$ ~10 nM) | IgG1 = 3 > 4 >> 2 | Monocytes, macrophages, activated neutrophils, dendritic cells? |
| FcγRIIA | H131 | Low to medium | IgG1 > 3 > 2 > 4 | Neutrophils, monocytes, macrophages, eosinophils, |
| | R131 | Low | IgG1 > 3 > 4 > 2 | dendritic cells, platelets |

TABLE 1-continued

Properties of Human FcγRs

| Fcγ variants | Allelic human | Affinity for IgG | Isotype preference | Cellular distribution |
|---|---|---|---|---|
| FcγRIIIA | V158 | Medium | IgG1 = 3 > > 4 > 2 | NK cells, monocytes, |
|  | F158 | Low | IgG1 = 3 > > 4 > 2 | macrophages, mast cells, eosinophils, dendritic cells? |
| FcγRIIB | I232 | Low | IgG1 = 3 = 4 > 2 | B cells, monocytes, |
|  | T232 | Low | IgG1 = 3 = 4 > 2 | macrophages, dendritic cells, mast cells |

An "immune response" refers to a biological response within a vertebrate against foreign agents, which response protects the organism against these agents and diseases caused by them. The immune response is mediated by the action of a cell of the immune system (for example, a T lymphocyte, B lymphocyte, natural killer (NK) cell, macrophage, eosinophil, mast cell, dendritic cell or neutrophil) and soluble macromolecules produced by any of these cells or the liver (including antibodies, cytokines, and complement) that results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal human cells or tissues.

An "immunomodulator" or "immunoregulator" refers to a component of a signaling pathway that may be involved in modulating, regulating, or modifying an immune response. "Modulating," "regulating," or "modifying" an immune response refers to any alteration in a cell of the immune system or in the activity of such cell. Such modulation includes stimulation or suppression of the immune system which may be manifested by an increase or decrease in the number of various cell types, an increase or decrease in the activity of these cells, or any other changes which can occur within the immune system. Both inhibitory and stimulatory immunomodulators have been identified, some of which may have enhanced function in a tumor microenvironment. In preferred embodiments of the disclosed invention, the immunomodulator is located on the surface of a T cell. An "immunomodulatory target" or "immunoregulatory target" is an immunomodulator that is targeted for binding by, and whose activity is altered by the binding of, a substance, agent, moiety, compound or molecule. Immunomodulatory targets include, for example, receptors on the surface of a cell ("immunomodulatory receptors") and receptor ligands ("immunomodulatory ligands").

"Immunotherapy" refers to the treatment of a subject afflicted with, or at risk of contracting or suffering a recurrence of, a disease by a method comprising inducing, enhancing, suppressing or otherwise modifying an immune response.

"Potentiating an endogenous immune response" means increasing the effectiveness or potency of an existing immune response in a subject. This increase in effectiveness and potency may be achieved, for example, by overcoming mechanisms that suppress the endogenous host immune response or by stimulating mechanisms that enhance the endogenous host immune response.

A "protein" refers to a chain comprising at least two consecutively linked amino acid residues, with no upper limit on the length of the chain. One or more amino acid residues in the protein may contain a modification such as, but not limited to, glycosylation, phosphorylation or disulfide bond formation. The term "protein" is used interchangeable herein with "polypeptide."

A "subject" includes any human or non-human animal. The term "non-human animal" includes, but is not limited to, vertebrates such as nonhuman primates, sheep, dogs, rabbits, rodents such as mice, rats and guinea pigs, avian species such as chickens, amphibians, and reptiles. In preferred embodiments, the subject is a mammal such as a nonhuman primate, sheep, dog, cat, rabbit, ferret or rodent. In more preferred embodiments of any aspect of the disclosed invention, the subject is a human. The terms, "subject" and "patient" are used interchangeably herein.

A "therapeutically effective amount" or "therapeutically effective dosage" of a drug or therapeutic agent, such as an Fc fusion protein of the invention, is any amount of the drug that, when used alone or in combination with another therapeutic agent, promotes disease regression evidenced by a decrease in severity of disease symptoms, an increase in frequency and duration of disease symptom-free periods, or a prevention of impairment or disability due to the disease affliction. A therapeutically effective amount or dosage of a drug includes a "prophylactically effective amount" or a "prophylactically effective dosage", which is any amount of the drug that, when administered alone or in combination with another therapeutic agent to a subject at risk of developing a disease or of suffering a recurrence of disease, inhibits the development or recurrence of the disease. The ability of a therapeutic agent to promote disease regression or inhibit the development or recurrence of the disease can be evaluated using a variety of methods known to the skilled practitioner, such as in human subjects during clinical trials, in animal model systems predictive of efficacy in humans, or by assaying the activity of the agent in in vitro assays.

By way of example, an anti-cancer agent promotes cancer regression in a subject. In preferred embodiments, a therapeutically effective amount of the drug promotes cancer regression to the point of eliminating the cancer. "Promoting cancer regression" means that administering an effective amount of the drug, alone or in combination with an anti-neoplastic agent, results in a reduction in tumor growth or size, necrosis of the tumor, a decrease in severity of at least one disease symptom, an increase in frequency and duration of disease symptom-free periods, a prevention of impairment or disability due to the disease affliction, or otherwise amelioration of disease symptoms in the patient. In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity, or other adverse physiological effects at the cellular, organ and/or organism level (adverse effects) resulting from administration of the drug.

By way of example for the treatment of tumors, a therapeutically effective amount or dosage of the drug preferably inhibits cell growth or tumor growth by at least about 20%, more preferably by at least about 40%, even more preferably by at least about 60%, and still more preferably by at least about 80% relative to untreated subjects. In the most preferred embodiments, a therapeutically effective amount or dosage of the drug completely inhibits cell growth or tumor growth, i.e., preferably inhibits cell growth or tumor growth by 100%. The ability of a compound to inhibit tumor growth can be evaluated in an animal model system, such as the CT26 colon adenocarcinoma, MC38 colon adenocarcinoma and Sa1N fibrosarcoma mouse tumor models described herein, which are predictive of efficacy in human tumors. Alternatively, this property of a composition can be evaluated by examining the ability of the compound to inhibit cell growth, such inhibition can be measured in vitro by assays known to the skilled practitioner. In other preferred embodiments of the invention, tumor regression may be observed and continue for a period of at least about 20 days, more preferably at least about 40 days, or even more preferably at least about 60 days.

"Treatment" or "therapy" of a subject refers to any type of intervention or process performed on, or administering an active agent to, the subject with the objective of reversing, alleviating, ameliorating, inhibiting, slowing down or preventing the onset, progression, development, severity or recurrence of a symptom, complication, condition or biochemical indicia associated with a disease.

Anti-CTLA-4 Antibodies with Enhanced ADCC are More Effective at Tumor Reduction

It is now recognized that CTLA-4 exerts its physiological function primarily through two distinct effects on the two major subsets of $CD4^+$ T cells: (1) down-modulation of helper T cell activity, and (2) enhancement of the immunosuppressive activity of regulatory T cells ($T_{regs}$). Lenschow et al. (1996) *Ann. Rev. Immunol.* 14:233; Wing et al. (2008) *Science* 322:271; Peggs et al. (2009) *J. Exp. Med.* 206:1717. $T_{regs}$ are known to constitutively express high levels of surface CTLA-4, and it has been suggested that this molecule is integral to their regulatory function. Takahashi et al. (2000) *J. Exp. Med.* 192:303; Birebent et al. (2004) *Eur. J. Immunol.* 34:3485. Accordingly, the $T_{reg}$ population may be most susceptible to the effects of CTLA-4 blockade. Studies of ipilimumab patients also show that responders, as distinguished from non-responders, exhibit decreased $T_{reg}$ infiltration after treatment, with depletion occurring via an ADCC mechanism and mediated by FcγRIIIA-expressing non-classical ($CD14^+CD16^{++}$) monocytes. Romano et al. (2014) *J. Immunotherapy of Cancer* 2(Suppl. 3):O14.

In one aspect, the present invention provides improved anti-CTLA-4 antibodies, such as improved forms of ipilimumab, having enhanced ADCC. Such antibodies would be expected to exhibit improved anti-tumor activity in light of recent experiments suggesting that tumor-specific depletion of regulatory T cell is an important component of ipilimumab's therapeutic efficacy. Such improved antibodies will retain their ability to block CD28 binding, and thus retain their ability to promote the anti-tumor activity of effector T cells.

Such improved antibodies may enhance therapeutic efficacy at a given dose, or may allow for lower dosing to attain any given level of efficacy, and thus reduced side effects. Alternatively, a dose may be selected at which the improved anti-CTLA-4 antibodies of the present invention, such as ipilimumab-GASDALIE, exhibit both improved anti-tumor efficacy and reduced side effect profile. Reduction of side effects may represent a significant advantage in light of the level of adverse events observed with anti-CTLA-4 therapy, particularly at higher doses. Ribas et al. (2013) *J. Clin. Oncology* 31:616; Feng et al. (2013) *Clin. Cancer* 19:3977.

Without intending to be limited by theory, first generation anti-CTLA-4 antibodies like ipilimumab, although therapeutically effective, may not promote maximal Fc receptor (FcR)-dependent $T_{reg}$ depletion at the tumor site. Ipilimumab is a human IgG1 antibody and may thus be a modest or poor mediator of Fc receptor (FcR)-dependent $T_{reg}$ depletion. In addition, side effects (including dose-limiting toxicities) of ipilimumab are caused by the blocking of CTLA-4/B7 interactions in $T_{eff}$ (and $T_{reg}$), leading to augmented $T_{eff}$ function, but are not caused by $T_{reg}$ depletion. Accordingly, an improved ipilimumab having increased $T_{reg}$ depletion activity, particularly in the tumor microenvironment, as provided by the present invention, will exhibit enhanced anti-tumor efficacy with no enhancement in adverse event profile. The net result is an improved therapeutic index.

Experiments in animal models have shown that anti-CTLA-4 antibodies with the greatest effector function are far more effective at reducing or preventing tumor growth. See Selby et al. (2013) *Cancer Immunol. Res.* 1:32 and commonly assigned WO 2014/089113 (selected figures of which are reproduced herein for convenience), the disclosures of which are hereby incorporated by reference in their entireties. Specifically, a mouse IgG2a anti-mouse CTLA-4 antibody, which had an A/I ratio of 70, was able to completely prevent tumor growth in the MC38 colon adenocarcinoma tumor model, whereas a mouse IgG2b anti-mouse CTLA-4 antibody, which had an A/I ratio of 7, was far less effective, as were IgG1 and IgG1/D265A antibodies. See FIGS. 2A-2E and FIGS. 3A-3B. See also FIG. 1A of Selby et al. (2013), which shows longer time courses, and demonstrating that 9 out of 9 animals treated with anti-CTLA-4-IgG2a remained tumor free, whereas only 1 of 10 animals treated with anti-CTLA-4-IgG2b remained tumor free.

Analogous experiments with the CT26 colon adenocarcinoma tumor model showed similar results (FIGS. 1A-1D), as did experiments with the syngeneic Sa1N fibrosarcoma tumor model (FIGS. 4A-4C and FIGS. 5A-5B).

Yet further experiments show that a non-fucosylated mouse IgG2b antibody, made by producing an anti-mouse CTLA-4 antibody in a CHO cell line lacking fucosyltransferase, has enhanced anti-tumor effects—similar to an IgG2a. FIGS. 6A-6F and FIGS. 7A-7B. Removal of fucose from heavy chain Asn297-linked oligosaccharides has been shown to enhance ADCC, based on improved binding to FcγRIIIa. Shields et al. (2002) *JBC* 277:26733; Niwa et al. (2005) *J. Immunol. Methods* 306: 151; Cardarelli et al. (2009) *Clin. Cancer Res.* 15:3376 (MDX-1401); Cardarelli et al. (2010) *Cancer Immunol. Immunotherap.* 59:257 (MDX-1342). The fact that enhancing ADCC activity by another mechanism (afucosylation as opposed to switching isotype) enhances anti-tumor activity suggests that enhanced ADCC activity per se is the property that leads to enhanced anti-tumor activity.

Other experiments demonstrate that mouse anti-CTLA-4 IgG2a depletes $T_{regs}$ in the tumor micro-environment but not in the periphery. See Selby et al. (2013) *Cancer Immunol. Res.* 1:32; WO 2014/089113. Such selective depletion would limit any undesired side effects, such as autoimmune responses, that might otherwise be expected if $T_{regs}$ were depleted generally. Such specific depletion would enhance the safety make it safer to administer $T_{reg}$-depleting anti-CTLA-4 antibodies of the present invention, such as ipilimumab GASDALIE, to subjects with autoimmune disorders or at risk of autoimmune disorders, e.g. to treat cancer in such subjects.

Thus, the mouse IgG2a isotype, which binds to activating FcRs and mediates ADCC, is effective in depleting T cells that preferentially express the target of the antibody, e.g., $T_{regs}$ at the tumor site that differentially express high levels of CTLA-4 compared to expression levels on CD8$^+$ and CD4$^+$ $T_{effs}$ at the tumor site. Collectively, these results suggest that anti-CTLA-4 antibodies, such as ipilimumab, having enhanced effector function would be more effective in treating cancer. Such antibodies would be expected to not only reduce CTLA-4 mediated signaling in effector T cells, but also to selectively deplete regulatory T cells in the tumor microenvironment that might otherwise suppress an anti-tumor immune response.

Additional experiments were performed to determine whether certain Fc modifications that increase ADCC would enhance the anti-tumor efficacy of anti-CTLA-4 antibodies in human systems, e.g. with anti-human CTLA-4, human Fcs and human Fc receptors. Some of these experiments involved use of the antigen binding domain of ipilimumab, an anti-human CTLA-4 antibody, rather than anti-mouse CTLA-4 mAb 9D9. Others of these experiments involved use of human heavy chain constant domain sequences comprising the Fc region, and were performed in transgenic mice expressing human, rather than mouse, Fcγ receptors. Smith et al. (2012) *Proc. Nat'l Acad. Sci.* (*USA*) 109:6181. For the experiments described herein, Fc receptor transgenic mice were bone marrow chimeras, rather than stable Fc receptor transgenic mice. Briefly, congenically marked B6 mice were irradiated and then allowed to reconstitute with bone marrow from human FcR transgenic mice.

Figure 8A:
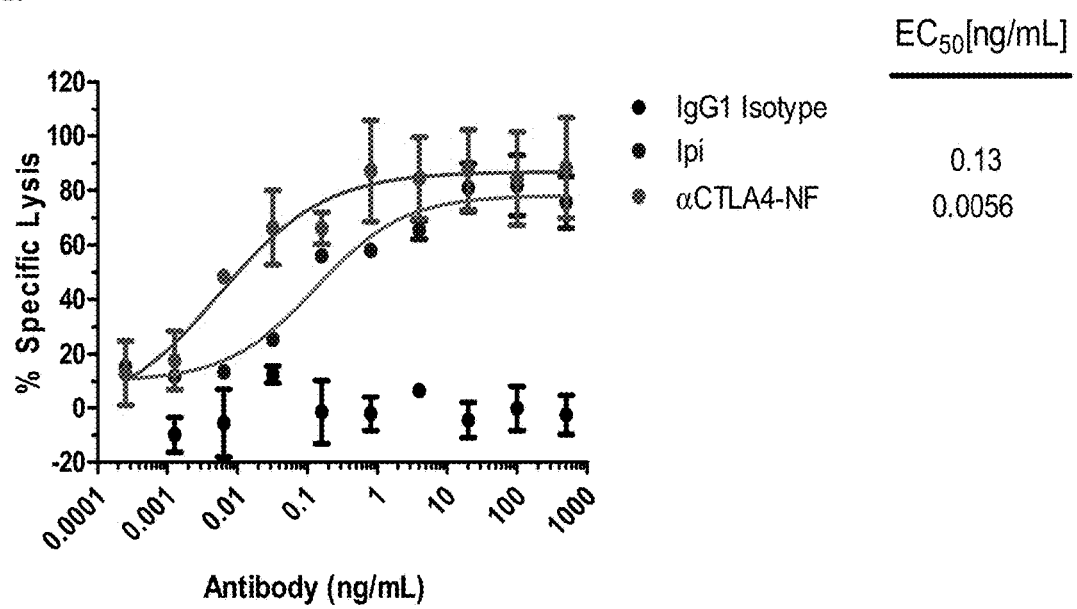
FIGS. 8A-8E show the effects of alternative Fc domains on specific NK-cell-mediated lysis of target cells.
Figure 8B:
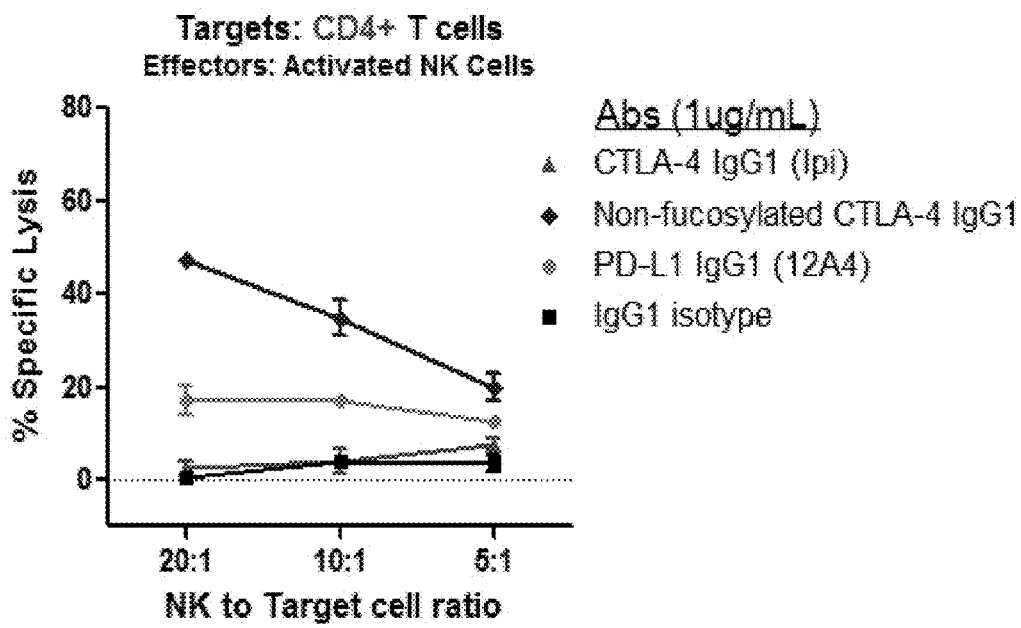
Figure 8C:
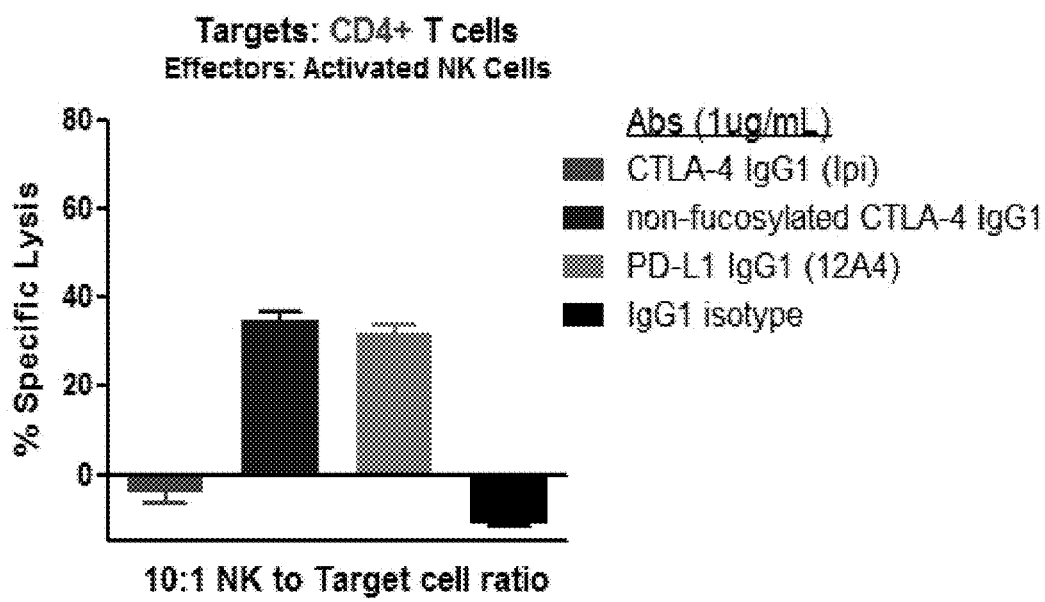
Figure 8D:
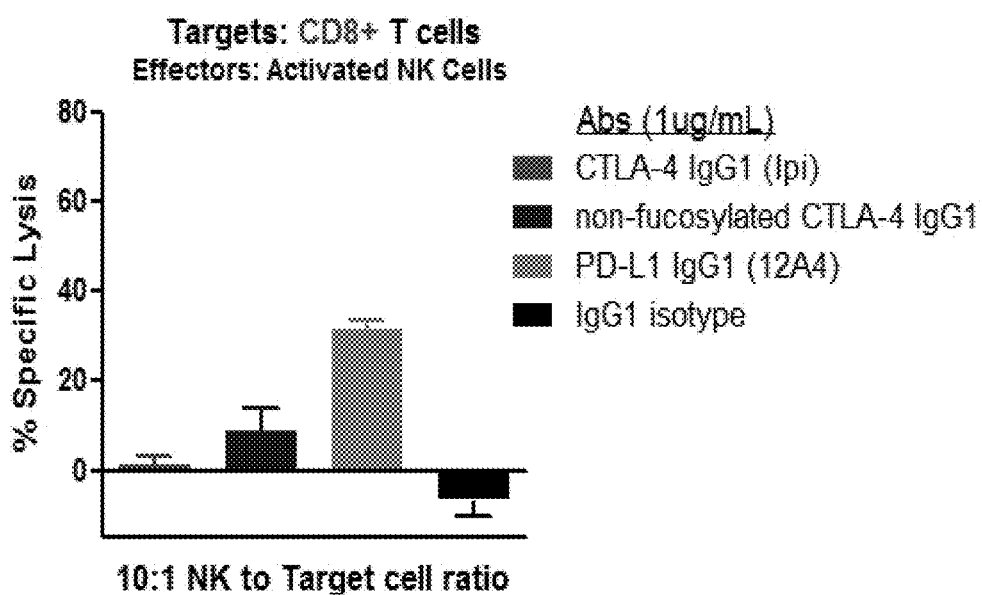
Figure 8E:
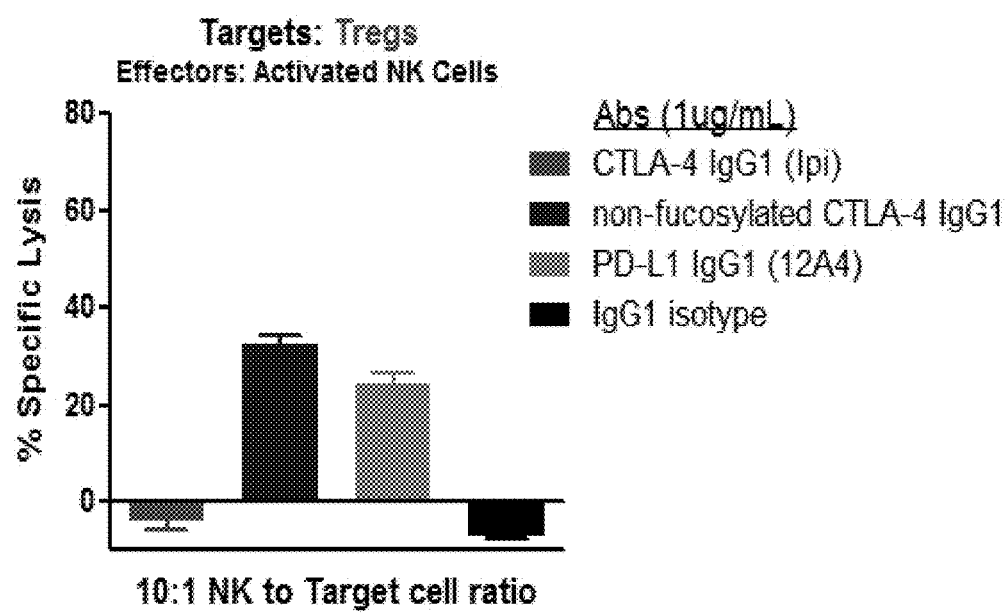
Figure 9A:
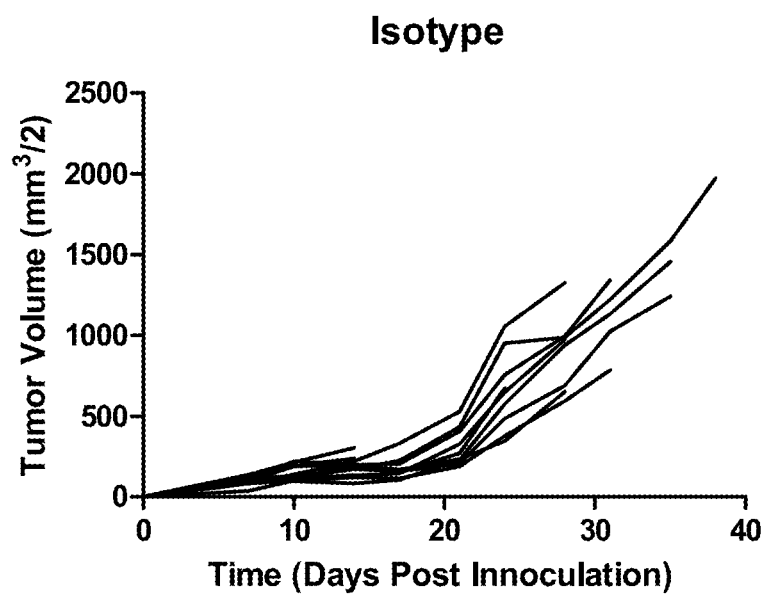
FIGS. 9A-9D show the anti-tumor activity of various antibodies (IgG1 isotype control, 9D9-hG1, 9D9-hG1nf and 9D9-hG1-GASDALIE, respectively) in an MC38 tumor model. See Example 7. The Fc regions on all antibodies were human or modifications thereof, and the mice were human Fc receptor transgenic mice. Smith et al. (2012) *Proc. Nat'l Acad. Sci. (USA)* 109:6181. Antibodies were administered seven days post-tumor. "9D9" antibodies had variable domains from anti-mouse CTLA-4 antibody 9D9. Both 9D9-hG1nf (non-fucosylated) and 9D9-hG1-GASDALIE were more effective than the IgG1 at inhibiting tumor growth, with 9/9 and 8/9 mice, respectively, being tumor-free (TF) at the end of the time course (as indicated in the upper right corners of the figures).
Figure 9B:
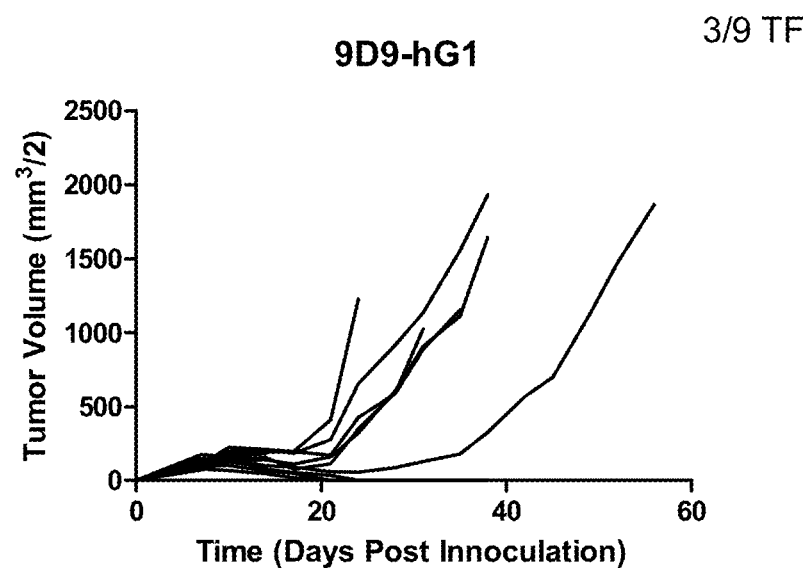
Figure 9C:
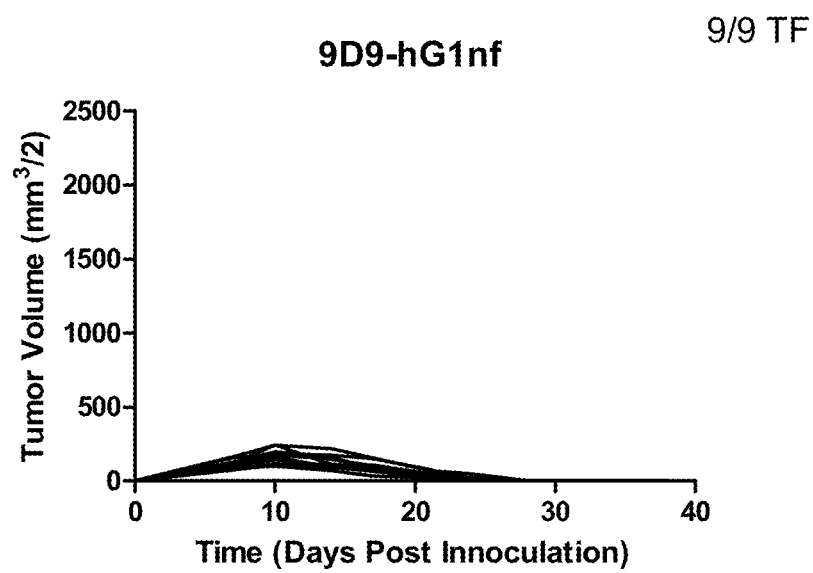
Figure 9D:
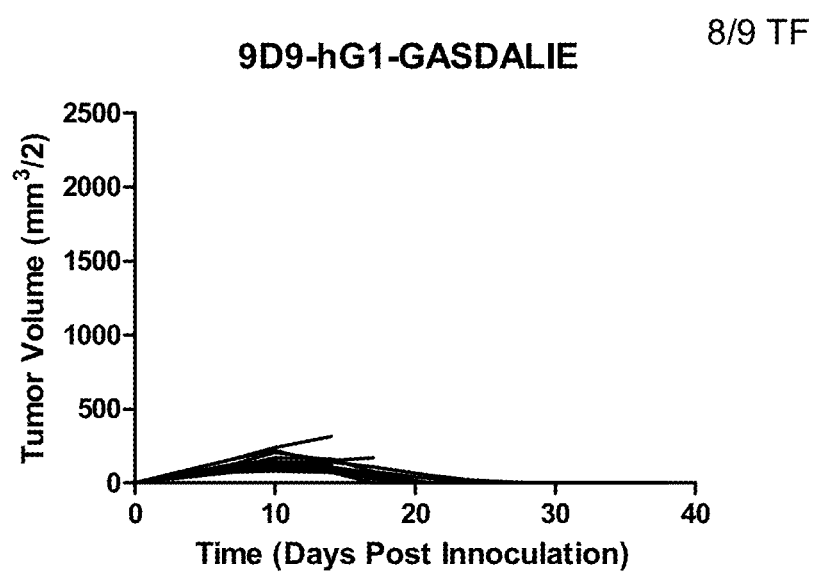
Figure 10A:
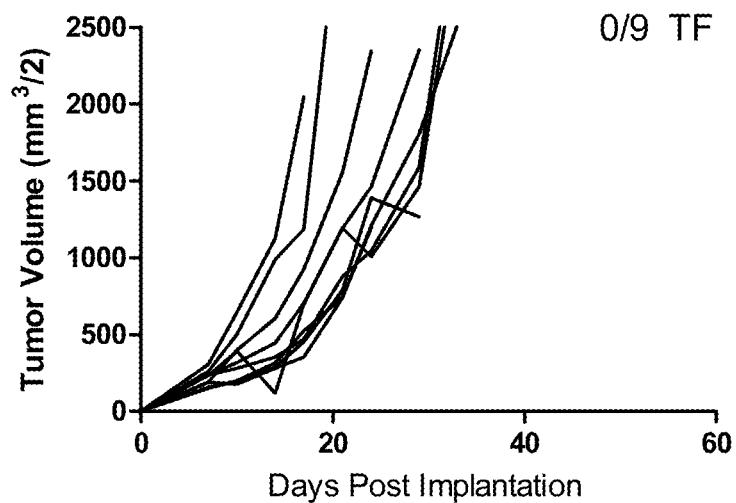
FIGS. 10A-10D show the anti-tumor activity of various antibodies (hIgG1 isotype control, 9D9 hIgG1, 9D9 hIgG1 NF and 9D9 hIgG1 GASDALIE, respectively) in an MC38 tumor model. Details were the same as for FIGS. 9A-9D except that antibodies were administered ten days post-tumor, rather than seven days. See Example 8. Both 9D9 hIgG1 NF (non-fucosylated) (FIG. 10C) and 9D9 hIgG1 GASDALIE (FIG. 10D) were more effective at inhibiting tumor growth than a 9D9 construct having an unmodified hIgG1 Fc region (FIG. 10B), with 6/9 and 5/9 mice, respectively, being tumor-free at the end of the time course.
Figure 10B:
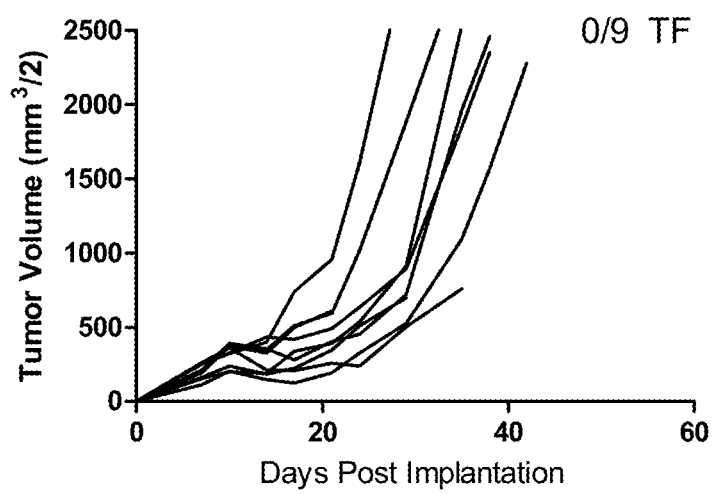
Figure 10C:
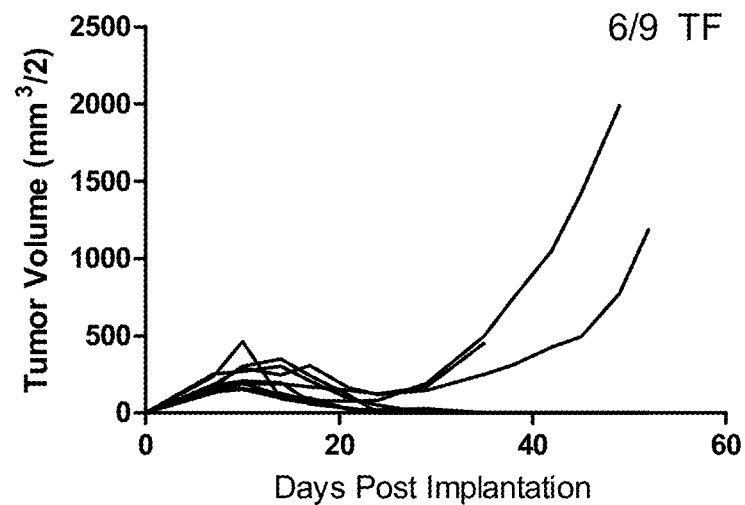
Figure 10D:
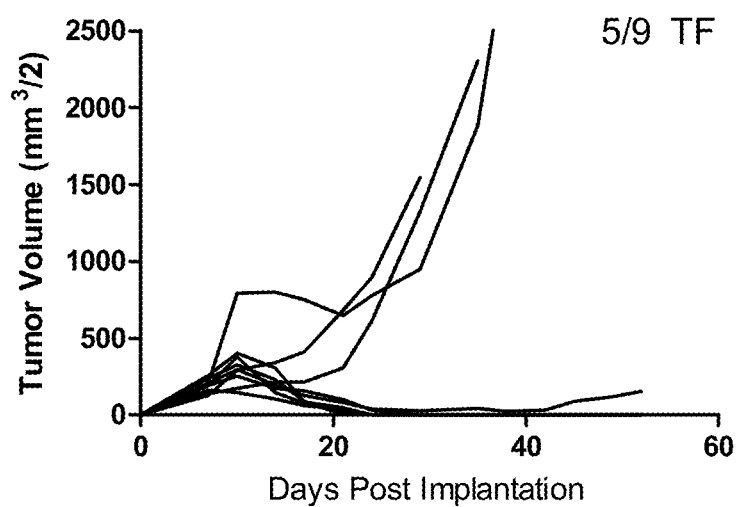

A non-fucosylated form of ipilimumab was shown to be more effective at eliciting NK92 cell based lysis of CD16-V158 (FcγRIII) cells, decreasing the EC$_{50}$ from 130 pg/mL to 5.6 pg/mL. See FIG. 8A. This same non-fucosylated ipilimumab was used in experiments involving lysis of CD4$^+$ T cells, CD8$^+$ T cells and $T_{regs}$ isolated from human samples by activated NK cells from those same human subjects. Non-fucosylated ipilimumab was significantly better than ipilimumab at inducing NK cell-mediated lysis of CD4$^+$ T cells and $T_{regs}$, but was less effective at eliciting lysis of CD8$^+$ T cells. Compare FIGS. 8C and 8E to FIG. 8D. This selectivity suggests that an anti-CTLA-4 antibody with enhanced effector function may be able to preferentially deplete $T_{regs}$ while largely sparing the CD8$^+$ effector T cells necessary for tumor eradication.

Both a non-fucosylated anti-mouse CTLA-4 antibody 9D9 having human IgG1 heavy chain constant domain and an anti-mouse CTLA-4 antibody 9D9 having human IgG1 heavy chain constant domain with GASDALIE mutations in the Fc region were effective in blocking tumor growth in the MC38 tumor model in human Fcγ receptor transgenic mice, whether administered 7 days or 10 days after tumor cell injection. See FIGS. 9A-9D and 10A-10D. These results demonstrate that the GASDALIE modifications enhance anti-tumor effects in a human Fc-human Fcγ receptor model.

Figure 11A:
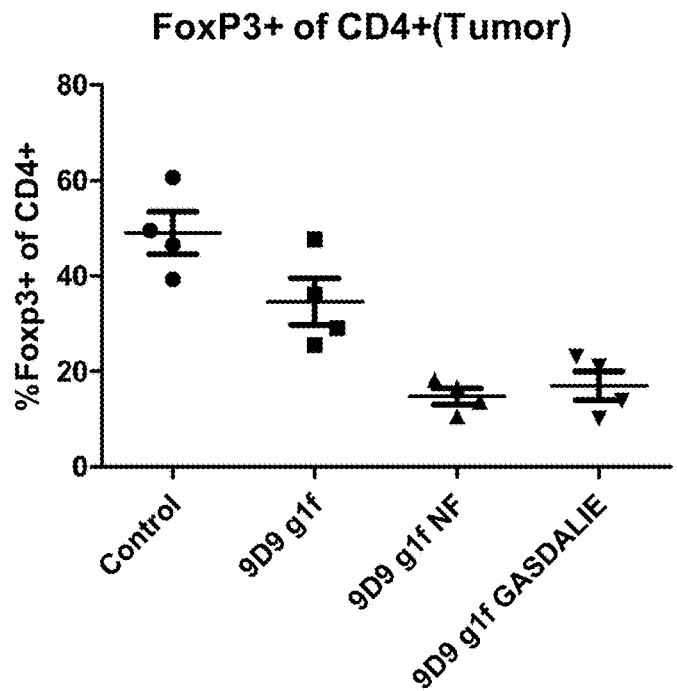
FIGS. 11A-11D show T cell infiltration in tumors in mice treated with various antibodies (IgG1 isotype control, 9D9 hIgG1, 9D9 hIgG1 NF and 9D9 hIgG1 GASDALIE, as indicated) in an MC38 tumor model. See Example 9.
Figure 11B:
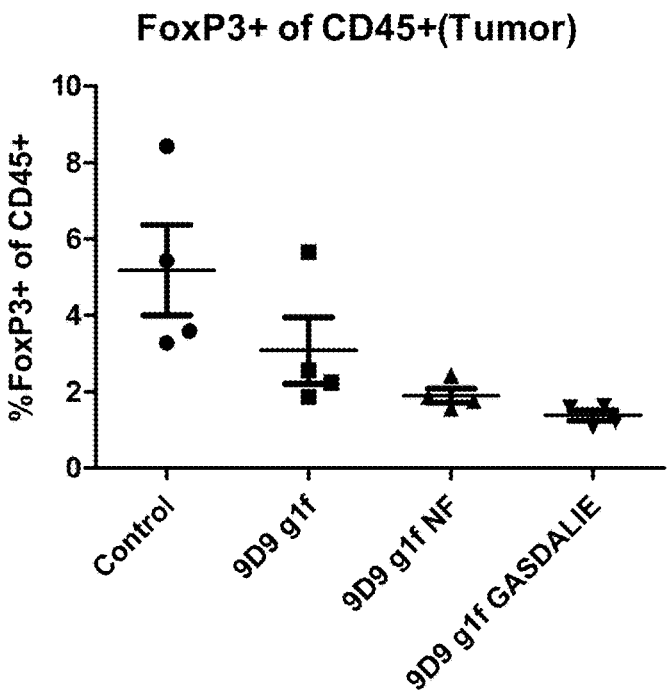
Figure 11C:
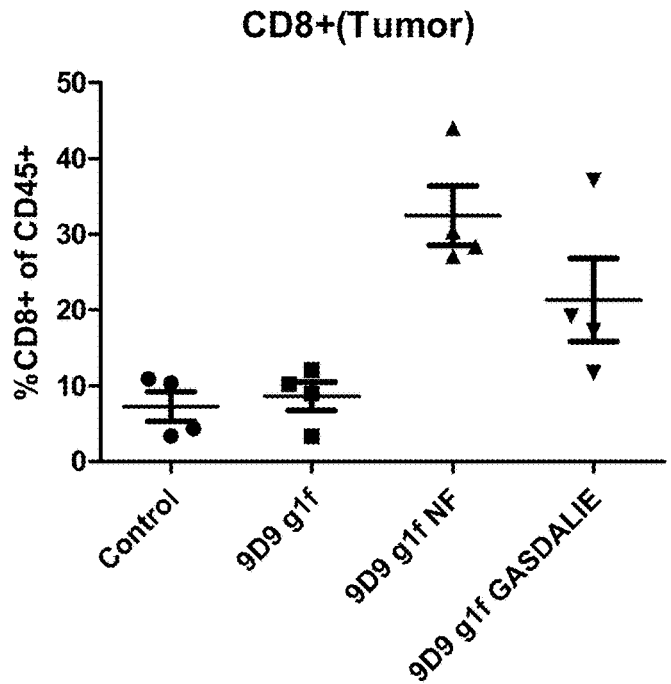
Figure 11D:
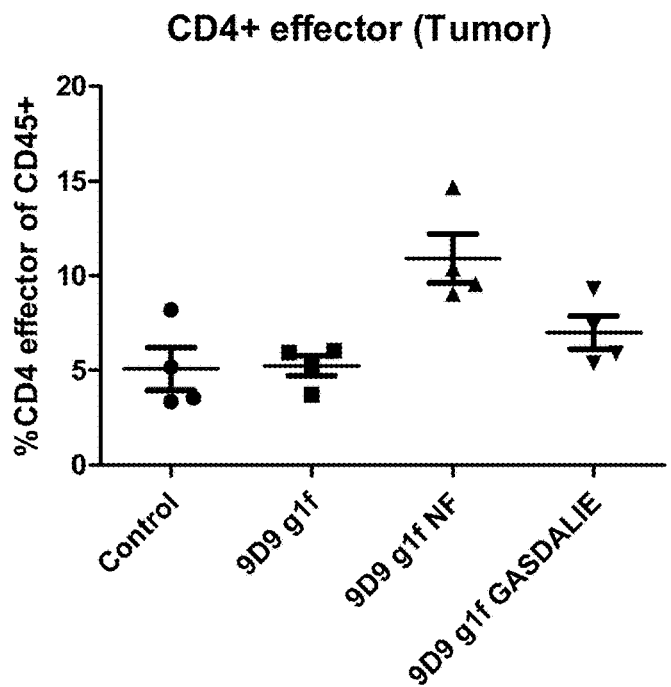

Tumor infiltrating T cells from mice treated with anti-CTLA-4 antibodies with enhanced effector function (9D9 huIgG1 NF and 9D9 huIgG1 GASDALIE) had a lower levels of $T_{regs}$ as a percentage of CD4$^+$ and CD45$^+$ T cells, but increased levels of CD8$^+$ T cells, compared with 9D9 huIgG1. See FIGS. 11A-11C. These results also suggest that such improved anti-CTLA-4 antibodies, including GASDALIE-modified Fc antibodies, would have enhanced anti-tumor efficacy, since they shift the T cell balance in the tumor away from immunosuppressive $T_{regs}$ and towards potentially tumor eradicating CD8$^+$ effector T cells.

Figure 12A:
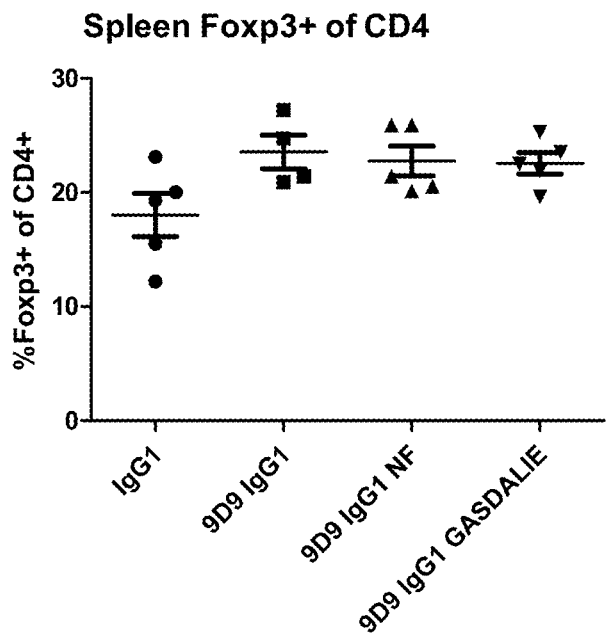
FIGS. 12A-12D show results analogous to those of FIGS. 11A-11D, except that data are provided for peripheral (spleen) T cells, rather than from tumors. See Example 10. In contrast to the results in FIGS. 11A and 11B, the data in FIGS. 12A and 12B show that peripheral $T_{regs}$ (Foxp3+) are not depleted by anti-CTLA-4 antibodies with enhanced effector function.
Figure 12B:
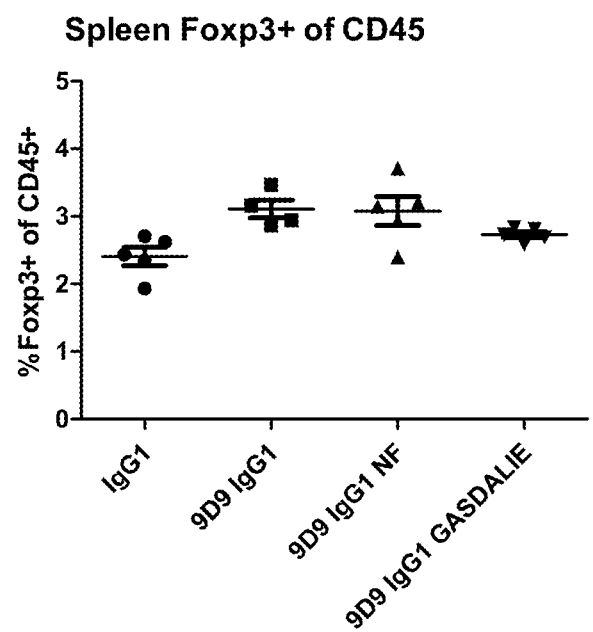
Figure 12C:
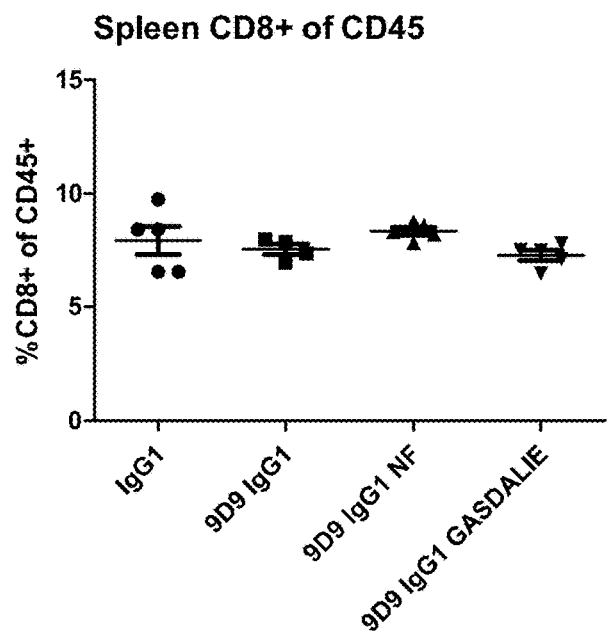
Figure 12D:
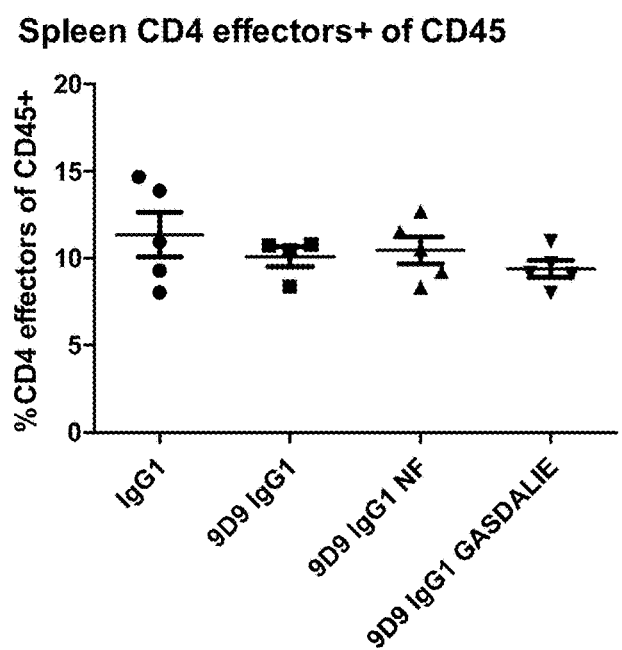

In contrast, anti-CTLA-4 antibodies with enhanced effector function did not reduce $T_{regs}$ in T cell populations from the spleens of these mice, and CD8$^+$ T cells were not increased, compared with 9D9 huIgG1. See FIGS. 12A-12C. This suggests that anti-CTLA-4 antibodies with enhanced effector function would not exhibit increased side effects, since depletion of regulatory cells appears to be limited to the tumor microenvironment, and does not occur in the periphery.

Improved Anti-CTLA-4 Antibodies with Enhanced Effector Functions, Such as Ipilimumab-GASDALIE In certain aspects of this invention, the improved anti-CTLA-4 antibody is a human IgG antibody. In certain embodiments of this human IgG antibody, binding to an FcγI, FcγIIa and/or FcγIIIa receptor is enhanced. In other embodiments, such enhanced binding to the FcγI, FcγIIa and/or FcγIIIa receptor results in increased ADCC. In certain preferred embodiments, enhanced binding of the modified Fc to the FcγI, FcγIIa and/or FcγIIIa receptor mediates a reduction of $T_{regs}$ at the tumor site. This reduction of $T_{regs}$ may be mediated by ADCC or a different mechanism that differentially reduces $T_{regs}$ at the tumor site but not in the periphery.

Various modifications to the Fc region of antibodies have been shown to enhance effector function. Isotype differences in antibodies have been demonstrated to have profound effects on the biological activity of antibodies. Nimmerjahn & Ravetch (2005) *Science* 310:1510; Nimmerjahn & Ravetch (2008) *Nat. Rev. Immunol.* 8:34; Nimmerjahn & Ravetch (2010) *Immunol. Rev.* 236:265. Anti-tumor activity of the TA99 antibody directed against the tumor-specific antigen, tyrosinase-related protein-1 (Tyrp1; gp75), was shown to require binding to the activating receptor FcRIV binding in the B16 murine melanoma model. Nimmerjahn & Ravetch (2005) *Science* 310:1510. Subsequent investigations have reached contradictory conclusions, with Bevaart et al. (2006) *Cancer Res.* 66:1261 finding a mandatory role for FcγRI, but no involvement of FcγRIII or FcγRIV, and Albanesi et al. (2012) *J. Immunol.* 189:5513 concluding that FcγRI and FcγRIII contributed to TA99 therapeutic effects, whereas FcγRIV did not. Interestingly, the anti-tumor activity of anti-CTLA-4 in the CT26, MC38 and Sa1N tumor models described herein (Examples 1, 2, and 3) implies the requirement for activating Fc receptors for anti-tumor activity. Enhanced binding to activating receptor and reduced binding to the inhibitory receptor correlates with the anti-tumor activity of the anti-CTLA-4 isotypes, with the following hierarchy: mIgG2a>>mIgG2b>>mIgG1D265A. This hierarchy follows the activity ratio of the binding of immunoglobulin Fc regions to activating Fc receptors versus inhibitory Fc receptors (known as the A/I ration) defined by Nimmerjahn & Ravetch (2005) *Science* 310:1510 and determined for antibodies mediating ADCC function.

Recently, IgG antibodies carrying the G236A, S239D, A330L and I332E ("GASDALIE") amino acid changes in their heavy chain constant region have been shown to exhibit dramatically enhanced binding to activating Fcγ receptors, resulting in enhanced cytotoxic effector function. Smith et al. (2012) *Proc. Nat'l Acad Sci.* (*USA*) 109:6181; Bournazos et al. (2014) *Cell* 158:1243. Experiments comparing non-fucosylated and GASDALIE modified IgG1f antibodies (human IgG1, 214R/356E/358M allotype) show enhanced binding to activating Fcγ receptors, as shown in Table 2, demonstrating their suitability for use in the anti-CTLA-4 antibodies of the present invention.

TABLE 2

Modified IgG1f Fc Regions - Fc Receptor Binding
$K_D$ Values (nM)

| Fcγ Receptor | IgG1f | IgG1f-NF | IgG1f-GASDALIE |
|---|---|---|---|
| CD16-V158 (FcγRIIIa) | 97 | 11 | 5 |
| CD32-H131 (FcγRIIa) | 530 | 560 | 78 |
| CD32-R131 (FcγRIIa) | 960 | 710 | 100 |
| CD32B (FcγRIIb) | — | — | 890 |
| CD64 (FcγRIa) | 0.2 | 0.1 | 0.6 |

Additional Potential Fc Modifications

In addition to addition of the GASDALIE mutations, Fc regions can be mutated to increase the affinity of IgG for the neonatal Fc receptor, FcRn, which prolongs the in vivo half-life of antibodies and results in increased anti-tumor activity. For example, introduction of M428L/N434S mutations into the Fc regions of bevacizumab (VEGF-specific) and cetuximab (EGFR-specific) increased antibody half-life in monkeys and improved anti-tumor responses in mice. Zalevsky et al. (2010) Nat. Biotechnol. 28:157.

The interaction of antibodies with FcγRs can also be enhanced by modifying the glycan moiety attached to each Fc fragment at the N297 residue. In particular, the absence of branching fucose residues strongly enhances ADCC via improved binding of IgG to activating FcγRIIIA without altering antigen binding or CDC. Natsume et al. (2009) Drug Des. Devel. Ther. 3:7. There is convincing evidence that afucosylated tumor-specific antibodies translate into enhanced therapeutic activity in mouse models in vivo. Nimmerjahn & Ravetch (2005) Science 310:1510; Mossner et al. (2010) Blood 115:4393.

Modification of antibody glycosylation can be accomplished by, for example, expressing the antibody in a host cell with altered glycosylation machinery. Cells with altered glycosylation machinery have been described in the art and can be used as host cells in which to express recombinant antibodies of this disclosure to thereby produce an antibody with altered glycosylation. For example, the cell lines Ms704, Ms705, and Ms709 lack the fucosyltransferase gene, FUT8 (α-(1,6) fucosyltransferase (see U.S. Pat. App. Publication No. 20040110704; Yamane-Ohnuki et al. (2004) Biotechnol. Bioeng. 87: 614), such that antibodies expressed in these cell lines lack fucose on their carbohydrates. As another example, EP 1176195 also describes a cell line with a functionally disrupted FUT8 gene as well as cell lines that have little or no activity for adding fucose to the N-acetylglucosamine that binds to the Fc region of the antibody, for example, the rat myeloma cell line YB2/0 (ATCC CRL 1662). PCT Publication WO 03/035835 describes a variant CHO cell line, Lec13, with reduced ability to attach fucose to Asn(297)-linked carbohydrates, also resulting in hypofucosylation of antibodies expressed in that host cell. See also Shields et al. (2002) J. Biol. Chem. 277:26733. Antibodies with a modified glycosylation profile can also be produced in chicken eggs, as described in PCT Publication No. WO 2006/089231. Alternatively, antibodies with a modified glycosylation profile can be produced in plant cells, such as Lemna. See e.g. U.S. Publication No. 2012/0276086. PCT Publication No. WO 99/54342 describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies. See also Umaña et al. (1999) Nat. Biotech. 17:176. Alternatively, the fucose residues of the antibody may be cleaved off using a fucosidase enzyme. For example, the enzyme alpha-L-fucosidase removes fucosyl residues from antibodies. Tarentino et al. (1975) Biochem. 14:5516.

Anti-CTLA-4 Antibodies

In certain embodiments, the anti-CTLA-4 antibody is ipilimumab or tremelimumab, or variants of these antibodies. Monoclonal antibodies that recognize and bind to the extracellular domain of CTLA-4 are described in U.S. Pat. No. 5,977,318, which is hereby incorporated by reference in its entirety. Human monoclonal antibodies of this disclosure can be generated using various methods, for example, using transgenic or transchromosomic mice carrying parts of the human immune system rather than the mouse system, or using in vitro display technologies such as phage or yeast display. See e.g. Bradbury et al. (2011) Nat. Biotechnol. 29(3):245. Transgenic and transchromosomic mice include mice referred to herein as the HUMAB MOUSE® (Lonberg et al. (1994) Nature 368:856) and KM MOUSE® (WO 02/43478), respectively. The production of exemplary human anti-human CTLA-4 antibodies of this disclosure is described in detail in U.S. Pat. Nos. 6,984,720 and 7,605,238, which are hereby incorporated by reference in their entireties. The human IgG1 anti-CTLA-4 antibody identified as 10D1 in these patents is also known as ipilimumab (also formerly known as MDX-010 and BMS-734016), which is marketed as YERVOY®. Other exemplary human anti-CTLA-4 antibodies of this disclosure are described in U.S. Pat. No. 6,682,736, which is hereby incorporated by reference in its entirety, including tremelimumab (formerly ticilimumab; CP-675,206), a human IgG2 anti-human CTLA-4 antibody.

Ipilimumab, a human anti-human CTLA-4 monoclonal antibody, has been approved for the treatment of metastatic melanoma and is in clinical testing in other cancers. Hoos et al. (2010) Semin. Oncol. 37:533; Hodi et al. (2010) N. Engl. J. Med. 363:711; Pardoll (2012) Nat. Immunol. 13(12): 1129. Ipilimumab has a human IgG1 isotype, which binds best to most human Fc receptors (Bruhns et al. (2009) Blood 113: 3716) and is considered equivalent to murine IgG2a with respect to the types of activating Fc receptors that it binds. Since IgG1 binds to the activating receptor CD16 (FcγRIIIa) expressed by human NK cells and monocytes, ipilimumab can mediate ADCC. The IgG1-isotype ipilimumab was originally isolated directly from a hybridoma but was subsequently cloned and expressed in Chinese hamster ovary (CHO) cells. Notwithstanding the consideration that an isotype that mediates ADCC and/or CDC might be undesirable in an antibody targeting a receptor on T cells that seeks to upregulate an immune response, the IgG1 isotype of the antibody was retained, in part, because it enhanced vaccine response in cynomolgus monkey and was considered functional. Ipilimumab has been shown to increase the numbers of activated T cells in the blood, as evidenced, for example, by a significant increase in the expression of HLA-DR on the surface of post-treatment CD4$^+$ and CD8$^+$ cells as well as increases in absolute lymphocyte count (Ku et al. (2010) Cancer 116:1767; Attia et al. (2005) J. Clin. Oncol. 23:6043; Maker et al. (2005) J. Immunol. 175:7746; Berman et al. (2009) J. Clin. Oncol. 27(suppl):15s.3020; Hamid et al. (2009) J. Clin. Oncol. 27(suppl): 15s.9008), indicating that depletion of T cells does not occur in the periphery in man. Ipilimumab demonstrated only modest levels of ADCC of activated T cells using IL-2-activated PBMCs as effector cells (unpublished); however, use of $T_{regs}$ as targets was not tested. Minor changes in peripheral $T_{reg}$ frequency in the blood of patients treated with ipilimumab have been observed (Maker et al. (2005) *J. Immunol.* 175:7746), but little information of the effect of ipilimumab on intratumoral $T_{regs}$ is available. However, a positive correlation between a high $CD8^+$ to $T_{reg}$ ratio and tumor necrosis in biopsies from metastatic melanoma lesions from patients treated with ipilimumab have been described. Hodi et al. (2008) *Proc. Nat'l Acad. Sci.* (*USA*) 105:3005. In addition, tumor tissue from ipilimumab-treated bladder cancer patients had lower percentages of $CD4^+$ $Foxp3^+$ T cells than tumors from untreated bladder cancer patients. Liakou et al. (2008) *Proc. Nat'l Acad. Sci.* (*USA*) 105:14987. These results are consistent with the data disclosed herein that ipilimumab mediates $T_{reg}$ reduction at the tumor site.

In contrast, tremelimumab is an IgG2 isotype, which does not bind efficiently to Fc receptors, except for the FcγRIIa variant H131. Bruhns et al. (2009) *Blood* 113:3716. While tremelimumab would have the ability to enhance T cell responses by blocking the inhibitory interactions between CTLA-4 and B7, the data disclosed herein suggests that tremelimumab may be limited in mediating depletion of $T_{regs}$ at the tumor and, on that basis, is expected to exhibit reduced anti-tumor activity compared to ipilimumab. It is has been difficult to directly compare the clinical activity of these two antibodies as the dosing regimens for each have been different. See e.g. Ascierto et al. (2011) *J. Transl. Med.* 9:196). Tremelimumab, like ipilimumab, has demonstrable anti-tumor activity. Ribas (2010) *Semin. Oncol.* 37(5):450. Interestingly, studies on the mechanism of action of tremelimumab show, in a limited number of samples analyzed by immunohistochemistry, that increases in tumor-infiltrating CD8 T cells occur as a result of therapy, while there is no change in the number of $Foxp3^+$ cells in the tumor after therapy. Comin-Anduix et al. (2008) *J. Transl. Med.* 6:22; Huang et al. (2011) *Clin. Cancer Res.* 17:4101. Alternatively, inhibition of $T_{reg}$ function may be accomplished by blocking CTLA-4/B7 interaction.

Additional Anti-CTLA-4 Antibodies and Uses

Additional anti-CTLA-4 antibody-related inventions are disclosed in the following commonly-assigned patent application publications, the disclosures of which are hereby incorporated by reference in their entireties: WO 1993/000431; WO 97/020574; WO 00/032231; WO 2001/014424; WO 2003/086459; WO 2005/003298; WO 2006/121168; WO 2007/056540; WO 2007/067959; WO 2008/109075; WO 2009/148915; WO 2010/014784; WO 2011/011027; WO 2010/042433; WO 2011/146382; WO 2012/027536; WO 2013/138702; WO 2009/089260; WO 2013/142796; and WO 2013/169971.

Targeted Antigen Binding

In various embodiments, the antibody of the present invention, e.g. ipilimumab-GASDALIE, is modified to selectively block antigen binding in tissues and environments where antigen binding would be detrimental, but allow antigen binding where it would be beneficial. In one embodiment, a blocking peptide "mask" is generated that specifically binds to the antigen binding surface of the antibody and interferes with antigen binding, which mask is linked to each of the binding arms of the antibody by a peptidase cleavable linker. See, e.g., U.S. Pat. No. 8,518,404 to CytomX. Such constructs are useful for treatment of cancers in which protease levels are greatly increased in the tumor microenvironment compared with non-tumor tissues. Selective cleavage of the cleavable linker in the tumor microenvironment allows disassociation of the masking/blocking peptide, enabling antigen binding selectively in the tumor, rather than in peripheral tissues in which antigen binding might cause unwanted side effects.

Alternatively, in a related embodiment, a bivalent binding compound ("masking ligand") comprising two antigen binding domains is developed that binds to both antigen binding surfaces of the (bivalent) antibody and interfere with antigen binding, in which the two binding domains masks are linked to each other (but not the antibody) by a cleavable linker, for example cleavable by a peptidase. See, e.g., Int'l Pat. App. Pub. No. WO 2010/077643 to Tegopharm Corp. Masking ligands may comprise, or be derived from, the antigen to which the antibody is intended to bind, or may be independently generated. Such masking ligands are useful for treatment of cancers in which protease levels are greatly increased in the tumor microenvironment compared with non-tumor tissues. Selective cleavage of the cleavable linker in the tumor microenvironment allows disassociation of the two binding domains from each other, reducing the avidity for the antigen-binding surfaces of the antibody. The resulting dissociation of the masking ligand from the antibody enables antigen binding selectively in the tumor, rather than in peripheral tissues in which antigen binding might cause unwanted side effects.

Nucleic Acid Molecules Encoding Antibodies of the Invention

Another aspect of the present disclosure pertains to isolated nucleic acid molecules that encode any of the improved anti-CTLA-4 antibodies of the present invention, such as ipilimumab-GASDALIE, that bind to targets, e.g., immunomodulatory receptors or ligands, on T cells. In preferred embodiments, these isolated nucleic acid molecules encode antibodies that target and block inhibitory immunomodulatory receptors. The nucleic acids may be present in whole cells, in a cell lysate, or in a partially purified or substantially pure form. The nucleic acid can be, for example, DNA or RNA, and may or may not contain intronic sequences. In certain embodiments, the DNA is genomic DNA, cDNA, or synthetic DNA, i.e., DNA synthesized in a laboratory, e.g., by the polymerase chain reaction or by chemical synthesis.

Pharmaceutical Compositions

Improved anti-CTLA-4 antibodies of the present invention, such as ipilimumab-GASDALIE, may be constituted in a composition, e.g., a pharmaceutical composition, containing the binding protein, for example an antibody or a fragment thereof, and a pharmaceutically acceptable carrier. As used herein, a "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, subcutaneous, intramuscular, parenteral, spinal or epidermal administration (e.g., by injection or infusion). A pharmaceutical composition of the invention may include one or more pharmaceutically acceptable salts, anti-oxidant, aqueous and non-aqueous carriers, and/or adjuvants such as preservatives, wetting agents, emulsifying agents and dispersing agents.

Dosage regimens are adjusted to provide the optimum desired response, e.g., a therapeutic response or minimal adverse effects. Typically, the dosage of an enhanced antibody of the disclosure required to achieve a certain level of anti-cancer efficacy is lower than for the unmodified antibody. Further, such a lower dosage typically results in a lower incidence or severity of adverse effects. For administration of an antibody of the disclosure that binds specifically to a target on a T cell, the dosage ranges from about 0.00001 to about 100 mg/kg, usually from about 0.0001 to about 20 mg/kg, and more usually from about 0.001 to about 10 mg/kg, of the subject's body weight. Preferably, the dosage is within the range of 0.01-10 mg/kg body weight. For example, dosages can be 0.01, 0.05, 0.1, 0.3, 1, 3, or 10 mg/kg body weight, and more preferably, 0.1, 0.3, 1, or 3 mg/kg body weight. The dosing schedule is typically designed to achieve exposures that result in sustained receptor occupancy based on typical pharmacokinetic properties of an antibody. An exemplary treatment regime entails administration once per week, once every two weeks, once every three weeks, once every four weeks, once a month, once every 3 months or once every three to 6 months. In one example, 3 mg/kg YERVOY® (ipilimumab) is administered intravenously over 90 minutes every three weeks for a total of four doses.

In a further embodiment, the anti-CTLA-4 antibody ipilimumab comprising an Fc region comprising GASDALIE (ipilimumab-GASDALIE) of the present invention is administered at a dose that is lower than the dose that is approved for ipilimumab. Such lower dosing may exhibit equivalent, or even enhanced, anti-tumor efficacy without significantly enhanced side effects when compared to treatment with unmodified ipilimumab. In exemplary embodiments, ipilimumab-GASDALIE is administered to treat unresectable or metastatic melanoma at less than 3 mg/kg, such as 2 mg/kg, 1 mg/kg, 0.5 mg/kg or lower. In other embodiments, ipilimumab-GASDALIE is administered for adjuvant treatment of patients with cutaneous melanoma with pathologic involvement of regional lymph nodes of more than 1 mm who have undergone complete resection, including total lymphadenectomy, at less than 10 mg/kg, such as 5 mg/kg, 3 mg/kg, 1 mg/kg, 0.5 mg/kg or lower.

Actual dosage levels of the active ingredients in the pharmaceutical compositions of the present invention may be varied so as to obtain an amount of the active ingredient that is effective to achieve the desired therapeutic response for a particular patient, composition, and mode of administration, without being unduly toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. One of ordinary skill in the art would be able to determine appropriate dosages based on such factors as the subject's size, the severity of the subject's symptoms, and the particular composition or route of administration selected. A composition of the present invention can be administered via one or more routes of administration using one or more of a variety of methods well known in the art.

Therapeutic Uses and Methods of the Invention

This disclosure provides methods for cancer immunotherapy, e.g. potentiating an endogenous immune response in a subject afflicted with a cancer so as to thereby treat the subject, which method comprises administering to the subject a therapeutically effective amount of any of the improved anti-CTLA-4 antibodies described herein.

In preferred embodiments of the present immunotherapeutic methods, the subject is a human.

Examples of other cancers that may be treated using the immunotherapeutic methods of the disclosure include bone cancer, pancreatic cancer, skin cancer, cancer of the head or neck, breast cancer, lung cancer, cutaneous or intraocular malignant melanoma, renal cancer, uterine cancer, ovarian cancer, colorectal cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, a hematological malignancy, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, environmentally induced cancers including those induced by asbestos, metastatic cancers, and any combinations of said cancers. In preferred embodiments, the cancer is selected from MEL, RCC, squamous NSCLC, non-squamous NSCLC, CRC, CRPC, squamous cell carcinoma of the head and neck, and carcinomas of the esophagus, ovary, gastrointestinal tract and breast. The present methods are also applicable to treatment of metastatic cancers.

Other cancers include hematologic malignancies including, for example, multiple myeloma, B-cell lymphoma, Hodgkin lymphoma/primary mediastinal B-cell lymphoma, non-Hodgkin's lymphomas, acute myeloid lymphoma, chronic myelogenous leukemia, chronic lymphoid leukemia, follicular lymphoma, diffuse large B-cell lymphoma, Burkitt's lymphoma, immunoblastic large cell lymphoma, precursor B-lymphoblastic lymphoma, mantle cell lymphoma, acute lymphoblastic leukemia, mycosis fungoides, anaplastic large cell lymphoma, T-cell lymphoma, and precursor T-lymphoblastic lymphoma, and any combinations of said cancers.

Combination Therapy

In certain embodiments of these methods for treating a cancer patient, the improved anti-CTLA-4 antibody of the present invention, e.g. ipilimumab-GASDALIE, is administered to the subject as monotherapy, whereas in other embodiments, stimulation or blockade of immunomodulatory targets may be effectively combined with standard cancer treatments, including chemotherapeutic regimes, radiation, surgery, hormone deprivation and angiogenesis inhibitors. The improved anti-CTLA-4 antibody can be linked to an anti-neoplastic agent (as an immunoconjugate) or can be administered separately from the agent. In the latter case (separate administration), the antibody can be administered before, after or concurrently with the agent or can be co-administered with other known therapeutic agents. Chemotherapeutic drugs include, among others, doxorubicin (ADRIAMYCIN®), cisplatin, carboplatin, bleomycin sulfate, carmustine, chlorambucil (LEUKERAN®), cyclophosphamide (CYTOXAN®; NEOSAR®), lenalidomide (REVLIMID®), bortezomib (VELCADE®), dexamethasone, mitoxantrone, etoposide, cytarabine, bendamustine (TREANDA®), rituximab (RITUXAN®), ifosfamide, vincristine (ONCOVIN®), fludarabine (FLUDARA®), thalidomide (THALOMID®), alemtuzumab (CAMPATH®, ofatumumab (ARZERRA®), everolimus (AFINITOR®, ZORTRESS®), and carfilzomib (KYPROLIS™). Co-administration of anti-cancer agents that operate via different mechanisms can help overcome the development of resistance to drugs or changes in the antigenicity of tumor cells.

Improved anti-CTLA-4 antibodies of the present invention, such as ipilimumab-GASDALIE, may also be used in combination with other immunomodulatory agents, such as antibodies against other immunomodulatory receptors or their ligands. Several other co-stimulatory and inhibitory receptors and ligands that regulate T cell responses have been identified. Examples of stimulatory receptors include Inducible T cell Co-Stimulator (ICOS), CD137 (4-1BB), CD134 (OX40), CD27, Glucocorticoid-Induced TNFR-Related protein (GITR), and HerpesVirus Entry Mediator (HVEM), whereas examples of inhibitory receptors include Programmed Death-1 (PD-1), B and T Lymphocyte Attenuator (BTLA), T cell Immunoglobulin and Mucin domain-3 (TIM-3), Lymphocyte Activation Gene-3 (LAG-3), adenosine A2a receptor (A2aR), Killer cell Lectin-like Receptor G1 (KLRG-1), Natural Killer Cell Receptor 2B4 (CD244), CD160, T cell Immunoreceptor with Ig and ITIM domains (TIGIT), and the receptor for V-domain Ig Suppressor of T cell Activation (VISTA). Mellman et al. (2011) *Nature* 480:480; Pardoll (2012) *Nat. Rev. Cancer* 12: 252; Baitsch et al. (2012) *PloS One* 7:e30852. Anti-PD-1 antibodies OPDIVO® (nivolumab) and KEYTRUDA® (pembrolizumab) have been approved for use in treating cancer, and may be combined with the improved anti-CLTA-4 antibodies of the present invention, e.g. ipilimumab-GASDALIE. These receptors and their ligands provide targets for therapeutics designed to stimulate, or prevent the suppression, of an immune response so as to thereby attack tumor cells. Weber (2010) *Semin. Oncol.* 37:430; Flies et al. (2011) *Yale J Biol. Med.* 84:409; Mellman et al. (2011) *Nature* 480:480; Pardoll (2012) *Nat. Rev. Cancer* 12:252. Stimulatory receptors or receptor ligands are targeted by agonist agents, whereas inhibitory receptors or receptor ligands are targeted by blocking agents. Among the most promising approaches to enhancing immunotherapeutic anti-tumor activity is the blockade of so-called "immune checkpoints," which refer to the plethora of inhibitory signaling pathways that regulate the immune system and are crucial for maintaining self-tolerance and modulating the duration and amplitude of physiological immune responses in peripheral tissues in order to minimize collateral tissue damage. See e.g. Weber (2010) *Semin. Oncol.* 37:430; Pardoll (2012) *Nat. Rev. Cancer* 12:252. Because many of the immune checkpoints are initiated by ligand-receptor interactions, they can be readily blocked by antibodies or modulated by recombinant forms of ligands or receptors.

The present invention is further illustrated by the following examples, which should not be construed as limiting. The contents of all figures and all references, patents and published patent applications cited throughout this application are expressly incorporated herein by reference.

Example 1

Anti-Tumor Activity of Variant Anti-CTLA-4 Isotypes in Murine CT26 Colon Adenocarcinoma Tumor Model To determine the relative potency of different isotypes of anti-CTLA-4 in anti-tumor activity, three of the four isotypic variants of anti-CTLA-4 antibody 9D9 (Peggs et al. (2009) *J. Exp. Med.* 206:1717) were generated (anti-CTLA-4-γ1D265A, anti-CTLA-4-γ2b, and anti-CTLA-4-γ2a, which bind equally well to CTLA-4+ cells) were tested together with a mouse IgG1 isotype control for anti-tumor activity in a syngeneic CT26 colon adenocarcinoma model. The control antibody used for the studies is a recombinant human anti-diphtheria toxin antibody with a mouse IgG1 isotype.

Ten BALB/c mice were subcutaneously injected with $1 \times 10^6$ CT26 tumor cells on day 0. Treatment was begun at Day 7 after implantation. Tumors were measured, randomized into treatment groups so as to have comparable mean tumor volumes (45-50 mm$^3$/2), and then treated intraperitoneally (IP) with the designated antibody (200 µg/dose) and again on Days 10, 14 and 17. Tumor volumes were measured twice weekly. Results are presented at FIGS. 1A-1D.

Example 2

Anti-Tumor Activity of Variant Anti-CTLA-4 Isotypes in MC38 Murine Colon Adenocarcinoma Tumor Model The anti-tumor activity of different anti-CTLA-4 isotypes was also assessed in a MC38 colon adenocarcinoma tumor model. C57BL/6 mice were each subcutaneously injected with $2 \times 10^6$ MC38 tumor cells. After 7 days, tumor volumes were determined and mice were randomized into treatment groups so as to have comparable mean tumor volumes (44.7-49.2 mm$^3$/2). Anti-CTLA-4 antibodies of four different isotypes (IgG1, IgG1D265A, IgG2a and IgG2b), formulated in PBS, were administered IP on Days 7, 10 and 14 at 200 µg per dose in a volume of 200 µl. Tumor volumes were recorded three times weekly. The changes in mean tumor volumes and median tumor volumes of the mice of groups treated with the different anti-CTLA-4 isotypes were also calculated. Results are presented at FIGS. 2A-2E and 3A-3B.

Example 3

Anti-Tumor Activity of Variant Anti-CTLA-4 Isotypes in an Immunogenic Sa1N Murine Fibrosarcoma Tumor Model The anti-tumor activity of anti-CTLA-4 was also assessed in an immunogenic Sa1N fibrosarcoma tumor model. A/J mice were subcutaneously injected with $2 \times 10^6$ Sa1N tumor cells. After 7 days, tumor volumes were determined and mice were randomized into treatment groups so as to have comparable mean tumor volumes (132.4-146.5 mm$^3$/2). Anti-CTLA-4 (9D9) antibodies having the IgG1, mutated IgG1D265A, and IgG2a isotypes were formulated in PBS and administered IP on Days 7, 11 and 14 at 200 µg per dose in a volume of 200 µl. Tumor volumes were recorded twice weekly. Results are presented at FIGS. 4A-4C and 5A-5B.

Example 4

Effect of Afucosylation on Anti-Tumor Activity of Variant Anti-CTLA-4 Isotypes in MC38 Tumor Model The anti-tumor activity of non-fucosylated (NF) anti-CTLA-4 (9D9) isotypes was assessed in the MC38 tumor model. These non-fucosylated variants were generated using a CHO cell line lacking fucosyltransferase for transfections. C57BL/6 mice were subcutaneously injected with $2 \times 10^6$ MC38 tumor cells per implant, and after 11 days mice were randomized into treatment groups having a mean tumor volume of about 230 mm$^3$/2. Anti-CTLA-4 antibodies of four different isotypes (IgG1D265A, IgG2a, IgG2a-NF, IgG2b and IgG2b-NF), were administered IP on Days 11, 13 and 15 at 200 µg per dose in a volume of 200 µl. Results are presented at FIGS. 6A-6F and 7A-7B.

Example 5

Anti-CTLA-4 Antibody Promotion of NK92-Mediated Cell Lysis Using Cell Lines

Non-fucosylated anti-human CTLA-4 antibodies, which exhibit enhanced effector function, were tested for their ability to promote NK92 cell-mediated lysis of 58 α-β-CTLA4 CD3 zeta cells using calcein release as a read-out, as follows. Briefly, NK92 cells were plated with calcein AM-labeled 58 α-β-CTLA4 CD3 zeta cells at a ratio of 5 to 1. A titration of unmodified ipilimumab or non-fucosylated ipilimumab was added to each well and cells were incubated for two hours. Calcein release was measured by reading the fluorescence intensity of the media using an Envision plate reader (Perkin Elmer). The percentage of antibody-dependent cell lysis was calculated based on mean fluorescence intensity (MFI) with the following formula: [(test MFI−mean background)/(mean maximum−mean background)]×100. Results are presented at FIG. 8A.

Example 6

Anti-CTLA-4 Antibody Promotion of NK-Mediated Cell Lysis Using Primary Human Cells Non-fucosylated anti-human CTLA-4 antibodies, which exhibit enhanced effector function, were tested for their ability to promote NK cell-mediated lysis of T cell subsets ($CD4^+$, $CD8^+$, $T_{regs}$) from human samples as follows. Briefly, T cell subsets for use as target cells were separated by negative selection using magnetic beads and activated for 72 hours. NK cells for use as effectors were separated by negative selection using magnetic beads and activated with IL-2 for 24 hrs. NK effector cells were mixed with calcein-labeled target T cells at 20:1, 10:1 or 5:1 ratios in the presence of antibody at 1 μg/ml for 2 hours. Calcein release was measured by reading the fluorescence intensity of the media using an Envision plate reader (Perkin Elmer). The percentage of antibody-dependent cell lysis was calculated based on mean fluorescence intensity (MFI) with the following formula: [(test MFI−mean background)/(mean maximum−mean background)]×100. Results are presented at FIGS. 8B-8E.

Example 7

MC38 Tumor Assay in Human Fc Receptor Transgenic Mice 7 Days Post-Tumor

Anti-mouse CTLA-4 antibodies (9D9) having human Fc regions with enhanced effector function were tested for their ability to reduce tumor growth in the MC38 tumor model in human Fc receptor transgenic mice as follows. C57BL/6 human FcR transgenic mice were each subcutaneously injected with $2 \times 10^6$ MC38 tumor cells. After 7 days, tumor volumes were determined and mice were randomized into treatment groups so as to have comparable mean tumor volumes. Anti-CTLA-4 antibodies of three different isotypes (IgG1, IgG1NF, IgG1 GASDALIE), formulated in PBS, were administered IP on Days 7, 10 and 14 at 200 μg per dose in a volume of 200 μl. Tumor volumes were recorded three times weekly. Results are presented at FIGS. 9A-9D.

Example 8

MC38 Tumor Assay in Human Fc Receptor Transgenic Mice 10 Days Post-Tumor

Anti-mouse CTLA-4 antibodies (9D9) having human Fc regions with enhanced effector function were tested for their ability to reduce tumor growth in the MC38 tumor model in human Fc receptor transgenic mice as described in Example 3, except that antibodies were dosed on days 10, 14 and 17 post-injection of tumor cells, rather than 7, 10 and 14 days post-injection. Results are presented at FIGS. 10A-10D.

Example 9

Tumor T Cell Infiltrates in MC38 Tumor Model

Tumor samples from the mice of Example 8 were obtained and used to evaluate the levels of $T_{regs}$, $CD4^+$ and $CD8^+$ T cells as follows. Briefly, all mice were sacrificed and tumor and spleen were harvested for analysis on Day 15 after tumor implantation. Single cell suspensions were prepared by dissociating tumor and spleen with the back of a syringe in a 24-well plate. Cell suspensions were passed through 70 μm filters, pelleted, resuspended, and counted. Cells were then plated in 96-well plates with $1 \times 10^6$ cells per well for staining. Cells were treated with 24G.2 (BioXcell), which blocks Fc binding to FcγRIIB and FcγRIII, and subsequently stained with antibodies against CD8 (clone 53-6.7; Biolegend), CD4 (clone GK1.5; Biolegend), and CD45 (clone 30-F11; Biolegend). For intracellular staining, samples were fixed, permeabilized, and stained with antibodies to Foxp3 (clone FJK-16s; eBioscience), Ki67 (clone SolA15; eBioscience), and CTLA-4 (clone 4F10; BD Pharmingen). Results are presented at FIGS. 11A-11D.

Example 10

$T_{reg}$ Levels in Peripheral Tissue

Spleens from the mice of Example 8 were obtained and used to evaluate the levels of $T_{regs}$, $CD4^+$, and $CD8^+$ T cells as described in Example 9. Results are presented at FIGS. 12A-12D.

TABLE 3

Summary of the Sequence Listing

| SEQ ID NO. | Description |
| --- | --- |
| 1 | human CTLA-4 (NP_005205.2) |
| 2 | human CD28 (NP_006130.1) |
| 3 | ipilimumab CDRH1 |
| 4 | ipilimumab CDRH2 |
| 5 | ipilimumab CDRH3 |
| 6 | ipilimumab CDRL1 |
| 7 | ipilimumab CDRL2 |
| 8 | ipilimumab CDRL3 |
| 9 | ipilimumab heavy chain variable domain |
| 10 | ipilimumab light chain variable domain |
| 11 | ipilimumab heavy chain |
| 12 | ipilimumab heavy chain w/o K448 |
| 13 | ipilimumab light chain |
| 14 | ipilimumab heavy chain + GASDALIE |
| 15 | ipilimumab heavy chain + GASDALIE w/o K448 |

With regard to antibody sequences, the Sequence Listing provides the sequences of the mature variable regions of the heavy and light chains, i.e. the sequences do not include signal peptides.

EQUIVALENTS

Those skilled in the art will recognize, or be able to ascertain using no more than routine experimentation, many equivalents of the specific embodiments disclosed herein. Such equivalents are intended to be encompassed by the following claims.

What is claimed is:

1. An anti-human CTLA-4 antibody comprising a heavy chain human IgG1 constant region comprising residues 236A, 239D, 330L and 332E according to the Kabat numbering system.

2. The antibody of claim 1 wherein the antibody comprises:
   a. a CDRH1 consisting of the sequence of SEQ ID NO: 3;
   b. a CDRH2 consisting of the sequence of SEQ ID NO: 4;
   c. a CDRH3 consisting of the sequence of SEQ ID NO: 5;
   d. a CDRL1 consisting of the sequence of SEQ ID NO: 6;
   e. a CDRL2 consisting of the sequence of SEQ ID NO: 7; and
   f. a CDRL3 consisting of the sequence of SEQ ID NO: 8.

3. The antibody of claim 2 wherein the antibody comprises:
   a. a heavy chain variable domain consisting of the sequence of SEQ ID NO: 9; and
   b. a light chain variable domain consisting of the sequence of SEQ ID NO: 10.

4. The antibody of claim 3 wherein the antibody comprises:
   a. a heavy chain consisting of the sequence of SEQ ID NO: 14; and
   b. a light chain consisting of the sequence of SEQ ID NO: 13.

5. The antibody of claim 3 wherein the antibody comprises:
   a. a heavy chain comprising the sequence of SEQ ID NO: 15; and
   b. a light chain comprising the sequence of SEQ ID NO: 13.

6. A method of treating cancer in a human subject comprising administering to the subject a therapeutic amount of an antibody of claim 1.

7. The method of claim 6 wherein the treatment or treating is performed in combination with one or more additional therapeutic agents.

8. The method of claim 6 wherein the cancer is unresectable or metastatic melanoma.

9. The method of claim 8 wherein the antibody is administered at a dose less than 3 mg/kg.

10. The method of claim 6 wherein the cancer is melanoma and the antibody is administered as an adjuvant to patients with cutaneous melanoma with pathologic involvement of regional lymph nodes of more than 1 mm who have undergone complete resection, including total lymphadenectomy.

11. The method of claim 10 wherein the antibody is administered at a dose less than 10 mg/kg.

* * * * *